United States Patent
Matsui

(10) Patent No.: US 11,877,046 B2
(45) Date of Patent: Jan. 16, 2024

(54) ENDOSCOPE, DRIVING METHOD, AND ENDOSCOPE SYSTEM

(71) Applicant: OLYMPUS CORPORATION, Tokyo (JP)

(72) Inventor: Yasunori Matsui, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 199 days.

(21) Appl. No.: 17/136,359

(22) Filed: Dec. 29, 2020

(65) Prior Publication Data

US 2021/0113074 A1    Apr. 22, 2021

Related U.S. Application Data

(63) Continuation of application No. PCT/JP2019/011451, filed on Mar. 19, 2019.

(30) Foreign Application Priority Data

Aug. 28, 2018  (JP) ................ 2018-159409

(51) Int. Cl.
*H04N 23/60* (2023.01)
*A61B 1/045* (2006.01)
(Continued)

(52) U.S. Cl.
CPC ....... *H04N 23/60* (2023.01); *A61B 1/000095* (2022.02); *A61B 1/045* (2013.01);
(Continued)

(58) Field of Classification Search
CPC ...... H04N 5/06; H04N 5/232; H04N 5/23245; H04N 2005/2255; A61B 1/000095;
(Continued)

(56) References Cited

U.S. PATENT DOCUMENTS

| 9,185,312  | B2 * | 11/2015 | Takei ................ A61B 1/00006 |
| 9,516,245  | B2 * | 12/2016 | Yokohama ............ H04N 25/42 |
| 2007/0159526 | A1 * | 7/2007 | Abe ....................... H04N 23/66 |
|            |      |         | 348/E5.043 |
| 2009/0290018 | A1 * | 11/2009 | Abe ....................... A61B 1/045 |
|            |      |         | 348/76 |

(Continued)

FOREIGN PATENT DOCUMENTS

| EP | 2407087 A2 * | 1/2012 |
| EP | 2407088 A2 * | 1/2012 |

(Continued)

OTHER PUBLICATIONS

International Search Report dated Jun. 18, 2019 issued in PCT/JP2019/011451.

*Primary Examiner* — Christopher S Kelley
*Assistant Examiner* — Asmamaw G Tarko
(74) *Attorney, Agent, or Firm* — Scully, Scott, Murphy & Presser, P.C.

(57) ABSTRACT

An endoscope includes: an imaging controller configured to drive in a first operation mode for operating an imager in accordance with an input first clock signal or in a second operation mode for operating the imager in accordance with an input second clock signal different from the first clock signal; a switch configured to output, to the imaging controller, a switching signal for switching the previously set second operation mode to be driven by the imaging controller to the first operation mode; and a first generator configured to generate a first enable signal causing the switch to output the switching signal based on the first clock signal when the first clock signal is input from an external processing device, and output the generated first enable signal to the switch.

16 Claims, 17 Drawing Sheets

(51) Int. Cl.
*H04N 5/06* (2006.01)
*A61B 1/00* (2006.01)
*G02B 23/24* (2006.01)
*H04N 23/667* (2023.01)
*H04N 23/50* (2023.01)

(52) U.S. Cl.
CPC ............... *G02B 23/24* (2013.01); *H04N 5/06* (2013.01); *H04N 23/667* (2023.01); *H04N 23/555* (2023.01)

(58) Field of Classification Search
CPC .... A61B 1/045; A61B 1/00009; G02B 23/24; H01J 2237/0044; H01J 2237/2007; H01J 2237/3321; H01J 2237/334; H01J 2237/3341; H01J 37/32174; H01J 37/32431; H01J 37/32568; H01J 37/32577; H01J 37/32633; H01J 37/32642; H01J 37/32715; H01L 21/67069; H01L 21/6831; H01L 21/68735
USPC ........................... 348/65, 222.1, 45, 372, 521
See application file for complete search history.

(56) References Cited

U.S. PATENT DOCUMENTS

| | | | |
|---|---|---|---|
| 2012/0016200 A1* | 1/2012 | Seto | A61B 1/0002 600/180 |
| 2012/0016201 A1* | 1/2012 | Seto | A61B 1/0653 600/180 |
| 2016/0360948 A1* | 12/2016 | Mizuno | H04N 23/125 |
| 2018/0098689 A1* | 4/2018 | On | A61B 1/00006 |
| 2019/0237863 A1* | 8/2019 | Miyazono | H01Q 1/46 |
| 2020/0221023 A1* | 7/2020 | Ono | H03L 7/0992 |

FOREIGN PATENT DOCUMENTS

| | | | |
|---|---|---|---|
| EP | 2868258 A1 * | 5/2015 | |
| JP | 2001218736 A * | 8/2001 | |
| JP | 2001-275957 A | 10/2001 | |
| JP | 2013-094269 A | 5/2013 | |
| JP | 2014-233387 A | 12/2014 | |
| JP | 2016-054878 A | 4/2016 | |
| JP | 6147097 B2 | 6/2017 | |
| WO | WO-2015033608 A1 * | 3/2015 | |
| WO | 2016/103878 A1 | 6/2016 | |

* cited by examiner

ENDOSCOPE, DRIVING METHOD, AND ENDOSCOPE SYSTEM

CROSS-REFERENCE TO RELATED APPLICATIONS

This application is a continuation of PCT international application No. PCT/JP2019/011451 filed on Mar. 19, 2019, which designates the United States, incorporated herein by reference, and which claims the benefit of priority from Japanese Patent Application No. 2018-159409, filed on Aug. 28, 2018, incorporated herein by reference.

BACKGROUND

1. Technical Field

The present disclosure relates to an endoscope that captures the inside of the body of a subject, a driving method, and a program.

2. Related Art

In the related art, there is a technique of an endoscope that performs a color conversion process on video data in accordance with the type of processor coupled and produces an output (see Japanese Patent No. 6147097). According to this technique, a system determining unit that determines the system of a processor is included in the endoscope including a primary color filter, and when the system determining unit determines that the coupled processor is compatible with a complementary color filter, a signal processing unit performs a color conversion process to convert the video data captured by the primary color filter from primary colors to complementary colors so as to output the video data corresponding to the processor.

SUMMARY

In some embodiments, an endoscope includes: an imaging controller configured to drive in a first operation mode for operating an imager in accordance with an input first clock signal or in a second operation mode for operating the imager in accordance with an input second clock signal different from the first clock signal; a switch configured to output, to the imaging controller, a switching signal for switching the previously set second operation mode to be driven by the imaging controller to the first operation mode; and a first generator configured to generate a first enable signal causing the switch to output the switching signal based on the first clock signal when the first clock signal is input from an external processing device, and output the generated first enable signal to the switch.

In some embodiments, provided is a driving method implemented by an endoscope including: an imaging controller configured to drive in a first operation mode for operating an imager in accordance with an input first clock signal or in a second operation mode for operating the imager in accordance with an input second clock signal different from the first clock signal; and a switch configured to output, to the imaging controller, a switching signal for switching the previously set second operation mode to be driven by the imaging controller to the first operation mode. The driving method includes: generating a first enable signal causing the switch to output the switching signal based on the first clock signal when the first clock signal is input from an external processing device; and outputting the generated first enable signal to the switch.

In some embodiments, an endoscope system includes a processing device and an endoscope including: an imaging controller configured to drive in a first operation mode for operating an imager in accordance with an input first clock signal or in a second operation mode for operating the imager in accordance with an input second clock signal different from the first clock signal; a switch configured to output, to the imaging controller, a switching signal for switching the previously set second operation mode to be driven by the imaging controller to the first operation mode; and a first generator configured to generate a first enable signal causing the switch to output the switching signal based on the first clock signal when the first clock signal is input from the processing device, and output the generated first enable signal to the switch.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
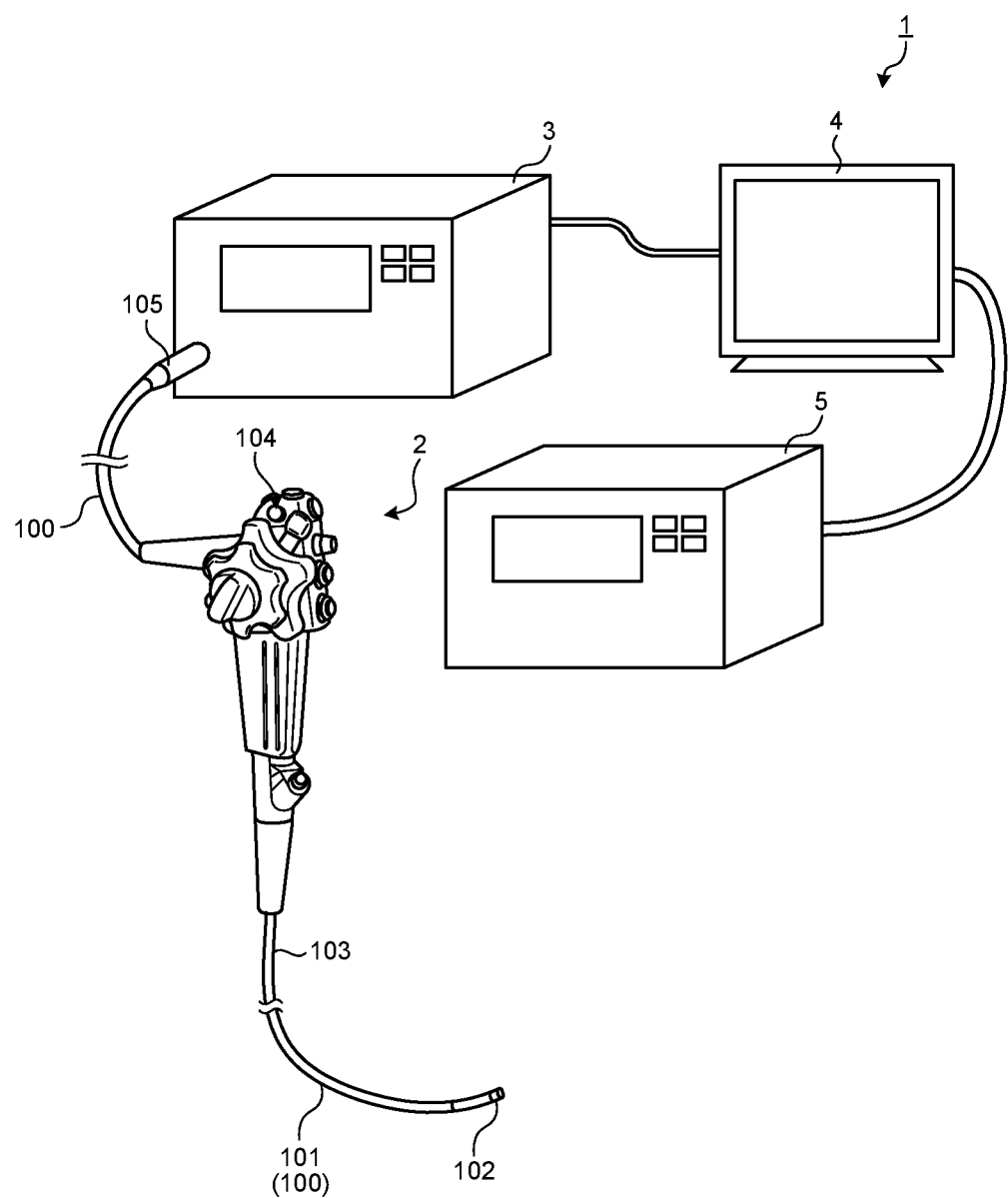
FIG. 1 is a schematic diagram illustrating a schematic configuration of an endoscope system according to a first embodiment.

Embodiments for carrying out the present disclosure are described below in detail with reference to the drawings. The present disclosure is not limited to the embodiments described below. In the drawings referred to in the description below, shapes, sizes, and positional relationships are merely illustrated in a schematic manner so as to understand the content of the present disclosure. That is, the present disclosure is not exclusively limited to the shapes, sizes, and positional relationships illustrated in the drawings. A medical endoscope system is described below.

First Embodiment

Configuration of Endoscope System

FIG. 1 is a schematic diagram illustrating a schematic configuration of an endoscope system according to a first embodiment. An endoscope system 1 illustrated in FIG. 1 includes an endoscope 2, a first processing device 3 (hereinafter simply referred to as the "new processor 3"), a display device 4, and a second processing device 5 (hereinafter simply referred to as the "old processor 5").

The endoscope 2 is detachably coupled to the new processor 3 or the old processor 5. With the endoscope 2, an insertion portion 101, which is a part of a transmission cable 100, is inserted into the body cavity of a subject. The endoscope 2 outputs, to the new processor 3 or the old processor 5, the imaging signal generated by capturing the inside of the body of the subject while the insertion portion 101 is inserted into the body cavity of the subject. In the endoscope 2, the one end side of the transmission cable 100, i.e., the size of a distal end portion 102 of the insertion portion 101 inserted into the body cavity of the subject, is provided with an imaging unit (imager) including an optical system and an imaging element described below, and the side of a proximal end side 103 of the insertion portion 101 is provided with an operating unit 104 that receives various operations on the endoscope 2. The imaging signal generated by the endoscope 2 is subjected to signal processing, converted into a video signal, and then transmitted to the new processor 3 or the old processor 5 via a connector 105 of the transmission cable 100 having a length of, for example, several meters. The detailed configuration of the endoscope 2 is described below.

The new processor 3 performs predetermined image processing on the video signal output from the coupled endoscope 2 and outputs the signal to the display device 4. The new processor 3 supplies, to the coupled endoscope 2, the illumination light to be emitted from the distal end portion 102 of the endoscope 2. The detailed configuration of the new processor 3 is described below.

The display device 4 presents the image corresponding to the video signal input from the new processor 3 or the old processor 5. The display device 4 presents various types of information regarding the endoscope system 1. The display device 4 is configured by using, for example, a liquid crystal or organic electro luminescence (EL) display panel.

The old processor 5 performs predetermined image processing on the video signal output from the coupled endoscope 2 and outputs the signal to the display device 4. The old processor 5 supplies, to the coupled endoscope 2, the illumination light to be emitted from the distal end portion 102 of the endoscope 2. The detailed configuration of the old processor 5 is described below.

Detailed Configuration of Endoscope System

Figure 2:
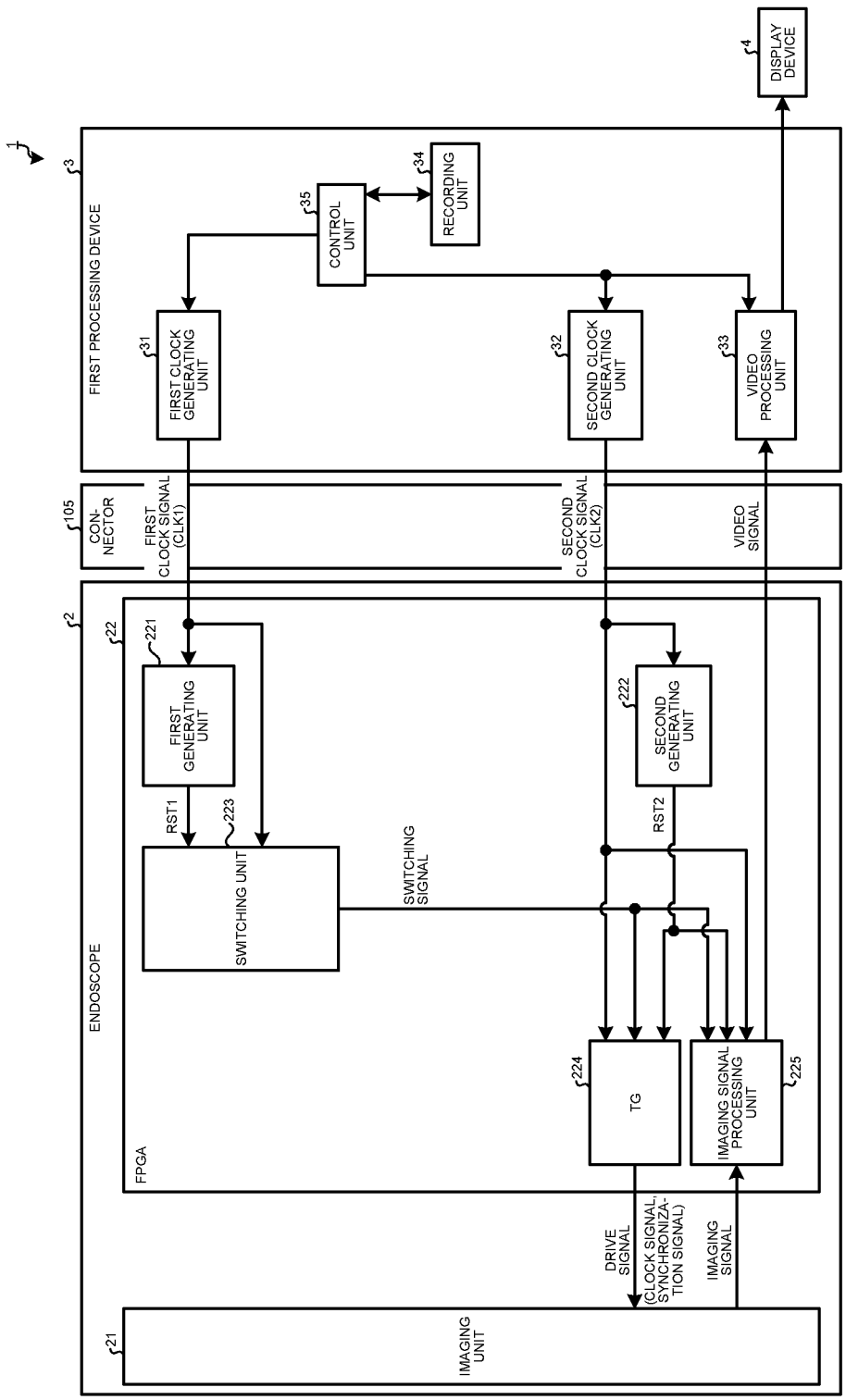
FIG. 2 is a block diagram illustrating a functional configuration in a state where an endoscope according to the first embodiment is coupled to a new processor.
Figure 3:
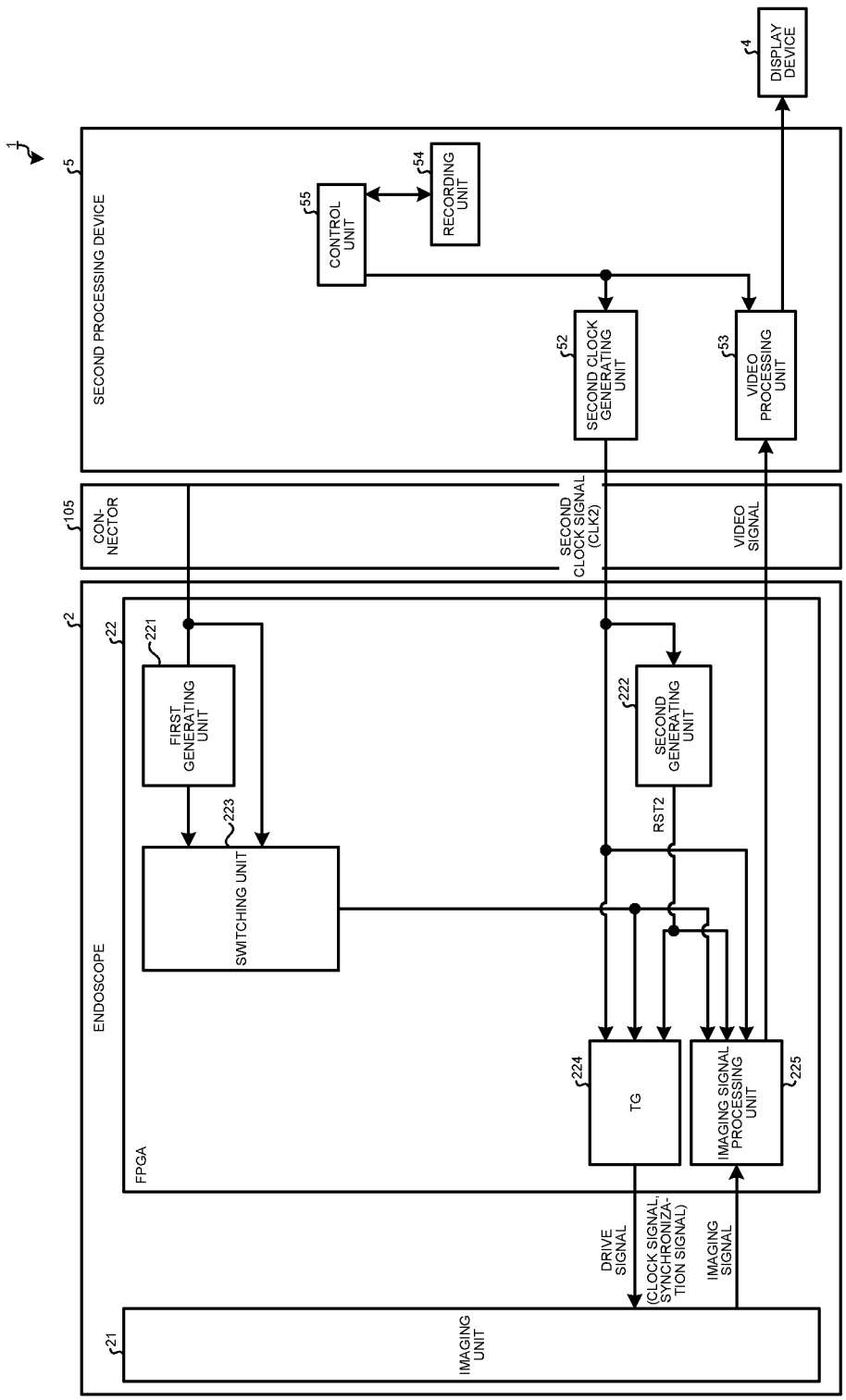
FIG. 3 is a block diagram illustrating a functional configuration in a state where the endoscope according to the first embodiment is coupled to an old processor.

Next, the functions of the relevant parts of the endoscope system 1 described above are described. FIG. 2 is a block diagram illustrating a functional configuration in a state where the endoscope 2 is coupled to the new processor 3. FIG. 3 is a block diagram illustrating a functional configuration in a state where the endoscope 2 is coupled to the old processor 5. After the functional configuration in a state where the endoscope 2 is coupled to the new processor 3 is described, the functional configuration in a state where the endoscope 2 is coupled to the old processor 5 is described below.

Configuration of Endoscope

First, the functional configuration of the endoscope 2 is described.

The endoscope 2 illustrated in FIG. 2 includes an imaging unit 21 and a field programmable gate array (FPGA) 22.

The imaging unit 21 is provided in the distal end portion 102 of the insertion portion 101. The imaging unit 21 captures the object based on a drive signal (e.g., a clock signal and a synchronization signal) input from the FPGA 22 described below to generate an imaging signal and then outputs the imaging signal to the FPGA 22. The imaging unit 21 is configured by using, for example, the optical system configured by using a plurality of lenses and a prism and a charge coupled device (CCD) or a complementary metal oxide semiconductor (CMOS) image sensor that receives the object image formed by the optical system, executes photoelectric conversion, generates an imaging signal, and then outputs the imaging signal.

The FPGA 22 switches between the operation modes of the endoscope 2 depending on the connection destination that is the new processor 3 or the old processor 5 and controls various operations regarding the endoscope 2. The FPGA 22 reads a program and various types of data from a memory (not illustrated) to control driving of the imaging unit 21 and driving of each unit of the endoscope 2. The FPGA 22 performs predetermined signal processing on the imaging signal input from the imaging unit 21 and outputs the signal to the new processor 3 or the old processor 5.

The FPGA 22 includes at least a first generating unit 221 (first generator), a second generating unit 222 (second generator), a switching unit 223 (switch), a timing generator (TG) 224, and an imaging signal processing unit 225.

The first generating unit 221 generates a first enable signal (RST1) for driving the switching unit 223 on the basis of a first clock signal (CLK1) input from the new processor 3 and outputs the first enable signal to the switching unit 223.

The second generating unit 222 generates a second enable signal (RST2) on the basis of a second clock signal (CLK2) input from the new processor 3 or the old processor 5 and outputs the second enable signal to the TG 224 and the imaging signal processing unit 225.

The switching unit 223 outputs, to the TG 224, the switching signal for switching the TG 224, which is previously set in a second operation mode, to a first operation mode. Specifically, the switching unit 223 generates the switching signal for switching the operation mode of the TG 224 from the second operation mode (old-processor coupling mode) to the first operation mode (new-processor coupling mode) based on the first enable signal input from the first generating unit 221 and the first clock signal input from the new processor 3 and outputs the generated switching signal to the TG 224 and the imaging signal processing unit 225 to switch the operation mode of the imaging unit 21.

The TG 224 drives the imaging unit 21 in the first operation mode (the new-processor coupling mode) in which the imaging unit 21 operates in accordance with the input first clock signal or in the second operation mode (the old-processor coupling mode) in which the imaging unit 21 operates in accordance with the input second clock signal that is different from the first clock signal. Specifically, the TG 224 generates the drive signal for driving the imaging unit 21 based on the switching signal input from the switching unit 223 and the second clock signal input from the new processor 3 or the old processor 5 and outputs the generated drive signal to the imaging unit 21. For example, when the switching signal is input from the switching unit 223, the TG 224 uses the second clock signal input from the new processor 3 to generate the drive signal that is processable in the operation mode of the new processor 3 and outputs the drive signal to the imaging unit 21. Conversely, when the switching signal is not input from the switching unit 223, the TG 224 uses the second clock signal input from the old processor 5 to generate the drive signal that is processable in the operation mode of the old processor 5 and outputs the generated drive signal to the imaging unit 21. The drive signal includes a clock signal and a synchronization signal for driving the imaging unit 21. When the signal patterns of a frame synchronization signal input from the old processor 5 and a frame synchronization signal input from the new processor 3 are different in a short pulse signal and a field pulse signal, the TG 224 performs the process to switch a receiving circuit for a frame synchronization signal (e.g., detect a rising edge exclusively or detects both the rising edge and the falling edge) in accordance with the first operation mode or the second operation mode or makes a change in accordance with a synchronization signal output timing operation mode to the imaging unit 21 in accordance with the synchronization signal output timing operation mode for the imaging unit 21 so that a video signal output timing for a video processing unit 33 may be a predetermined timing in consideration of the processing delay time difference corresponding to the operation mode in the imaging signal processing unit 225. The synchronization signal to the imaging unit 21 is transmitted in the identical signal line by, for example, separating code patterns, a vertical synchronization signal code and a horizontal synchronization signal code, as a digital signal. According to the first embodiment, the TG 224 functions as an imaging controller.

The imaging signal processing unit 225 performs, on the imaging signal input from the imaging unit 21, signal processing corresponding to the first operation mode (the new-processor coupling mode) for the operation in accordance with the input first clock signal or, on the imaging signal input from the imaging unit 21, signal processing corresponding to the second operation mode (the old-processor coupling mode) for the operation in accordance with the input second clock signal different from the first clock signal. Specifically, the imaging signal processing unit 225 performs predetermined signal processing on the imaging signal input from the imaging unit 21 based on the switching signal input from the switching unit 223 and the second clock signal input from the new processor 3 or the old processor 5 to generate a video signal and outputs the video signal to the new processor 3 or the old processor 5. For example, when the switching signal is input from the switching unit 223, the imaging signal processing unit 225 performs signal processing on the imaging signal to generate a video signal that is processable by the new processor 3 and outputs the video signal to the new processor 3. Conversely, when the switching signal is not input from the switching unit 223, the imaging signal processing unit 225 performs signal processing on the imaging signal to generate a video signal that is processable by the old processor 5 and outputs the video signal to the old processor 5. Examples of the signal processing include noise reduction/correction processing, format conversion processing, A/D conversion processing, imaging signal amplification processing, and color conversion processing. The imaging signal processing unit 225 uses the switching signal to switch execution/inexecution of pixel defect correction processing during the above-described noise reduction/correction processing, switches execution/inexecution of color space conversion (from RGB to CMY), from progressive conversion to interlace conversion (PI conversion), or from interlace conversion to progressive conversion (IP conversion) during the above-described format conversion processing, switch execution/inexecution of conversion from an RGB color space imaging signal to a complementary (CMY) color space imaging signal during the above-described color conversion processing, and switch a predetermined amplification factor during the above-described imaging signal amplification processing.

Configuration of New Processor

Next, the functional configuration of the new processor 3 is described.

The new processor 3 includes a first clock generating unit 31, a second clock generating unit 32, a video processing unit 33, a recording unit 34, and a control unit 35.

The first clock generating unit 31 generates the first clock signal (CLK1) having a predetermined frequency and outputs the first clock signal to the endoscope 2 under the control of the control unit 35. The first clock generating unit 31 is configured by using, for example, a clock generator.

The second clock generating unit 32 generates the second clock signal (CLK) having a predetermined frequency and outputs the second clock signal to the endoscope 2 under the control of the control unit 35. The second clock generating unit 32 is configured by using, for example, a clock generator. The first clock signal and the second clock signal may have the identical frequency or the identical clock or may have different frequencies or clocks.

The video processing unit 33 performs predetermined video processing on the video signal input from the endoscope 2 and outputs the signal to the display device 4. The predetermined video processing is, for example, white balance adjustment processing, gain-up adjustment processing, demosaicing processing, format conversion processing, or the like. The video processing unit 33 is configured by using a graphics processing unit (GPU), a digital signal processing (DSP), an application specific integrated circuit (ASIC), or the like.

The recording unit 34 stores various programs executed by the endoscope system 1, data in processing, and image data corresponding to a video signal. The recording unit 34 is configured by using a volatile memory, a non-volatile memory, a memory card, or the like.

The control unit 35 controls each unit of the endoscope system 1. The control unit 35 is configured by using, for example, a central processing unit (CPU).

Configuration of Old Processor

Next, the functional configuration of the old processor 5 is described.

The old processor 5 illustrated in FIG. 3 has the configuration except for the first clock generating unit 31 of the new processor 3 described above. Specifically, the old processor 5 includes a second clock generating unit 52, a video processing unit 53, a recording unit 54, and a control unit 55.

The second clock generating unit 52 generates the second clock signal (CLK) having a predetermined frequency and outputs the second clock signal to the endoscope 2 under the control of the control unit 55. The second clock generating unit 52 is configured by using, for example, a clock generator.

The video processing unit 53 performs predetermined video processing on the video signal input from the endoscope 2 and outputs the signal to the display device 4. The video processing unit 53 is configured by using a GPU, a DSP, an ASIC, or the like.

The recording unit 54 stores various programs executed by the endoscope system 1, data in processing, and the image data corresponding to a video signal. The recording unit 54 is configured by using a volatile memory, a non-volatile memory, a memory card, or the like.

The control unit 55 controls each unit of the endoscope system 1. The control unit 55 is configured by using, for example, a CPU.

Process of Endoscope

Figure 4:
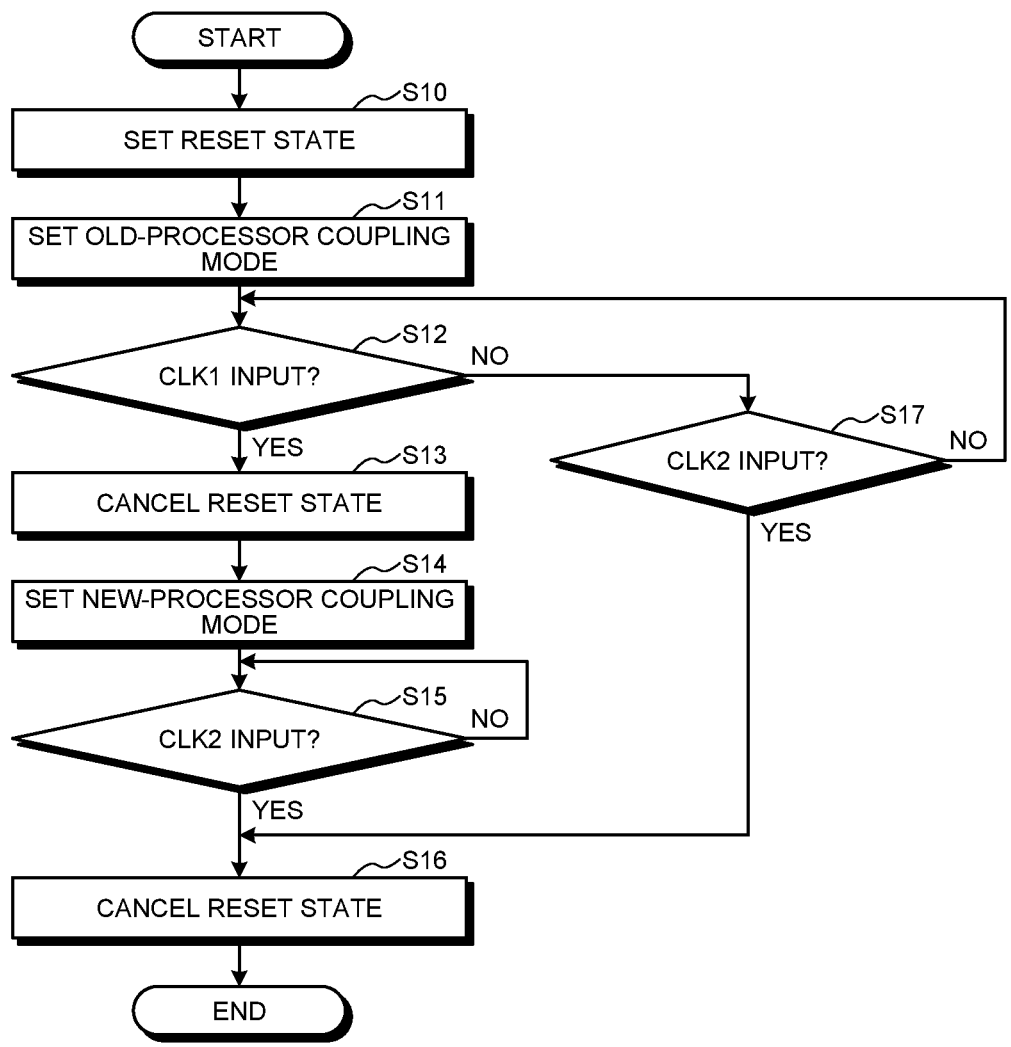
FIG. 4 is a flowchart illustrating the overview of a process performed by the endoscope according to the first embodiment.

Next, a process performed by the endoscope 2 is described. FIG. 4 is a flowchart illustrating the overview of the process performed by the endoscope 2.

As illustrated in FIG. 4, first, when the power of the endoscope 2 is activated, the first generating unit 221 and the second generating unit 222 each set their own states to a reset state (Step S10), and the switching unit 223 sets the operation mode to the old-processor coupling mode that is the second operation mode (Step S11).

Subsequently, when the endoscope 2 is coupled to the new processor 3 and thus the first clock signal (CLK1) is input from the new processor 3 (Step S12: Yes), the endoscope 2 proceeds to Step S13 described below. Conversely, when the endoscope 2 is not coupled to the new processor 3 but is coupled to the old processor 5, the first clock signal (CLK1) is not input from the new processor 3 (Step S12: No), and the second clock signal (CLK2) is not also input (Step S17: No), the endoscope 2 returns to S12 described above. When the first clock signal (CLK1) is not input from the new processor 3 (Step S12: No) and the second clock signal (CLK2) is input (Step S17: Yes), the endoscope 2 proceeds to S16 described below.

At Step S13, the first generating unit 221 cancels the reset state based on the first clock signal (CLK1) input from the new processor 3 to generate and output the first enable signal (RST1) to the switching unit 223.

Subsequently, the switching unit 223 generates the switching signal for switching the imaging unit 21, the TG 224, and the imaging signal processing unit 225 to the new-processor coupling mode, which is the first operation mode, based on the first enable signal input from the first generating unit 221 and the first clock signal input from the new processor 3 and outputs the generated switching signal to the TG 224 and the imaging signal processing unit 225 so as to set the new-processor coupling mode, which is the first operation mode, for the imaging unit 21, the TG 224, and the imaging signal processing unit 225 (Step S14). After Step S14, the endoscope 2 proceeds to Step S15.

Then, when the second clock signal (CLK2) is input from the new processor 3 or the old processor 5 (Step S15: Yes), the endoscope 2 proceeds to Step S16 described below. Conversely, when the second clock signal (CLK2) is not input from the new processor 3 or the old processor 5 (Step S15: No), the endoscope 2 waits until the second clock signal (CLK2) is input.

At Step S16, the second generating unit 222 cancels the reset state based on the second clock signal to generate and output the second enable signal (RST2) to the TG 224 and the imaging signal processing unit 225. After Step S16, the endoscope 2 ends this process. Accordingly, the endoscope 2 enters a state to enable the examination of the subject.

Operation Timing of Each Unit of Endoscope

Figure 5:
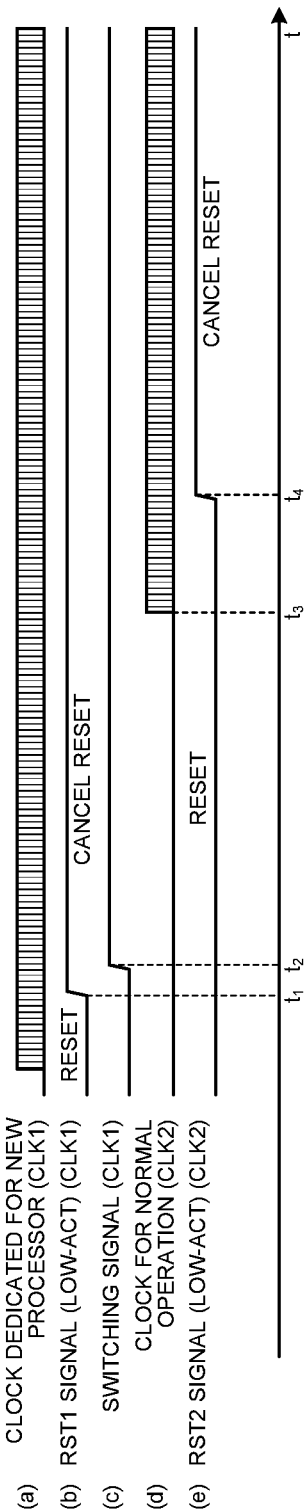
FIG. 5 is a timing chart illustrating the operation of each unit when the endoscope according to the first embodiment is coupled to the new processor.
Figure 6:
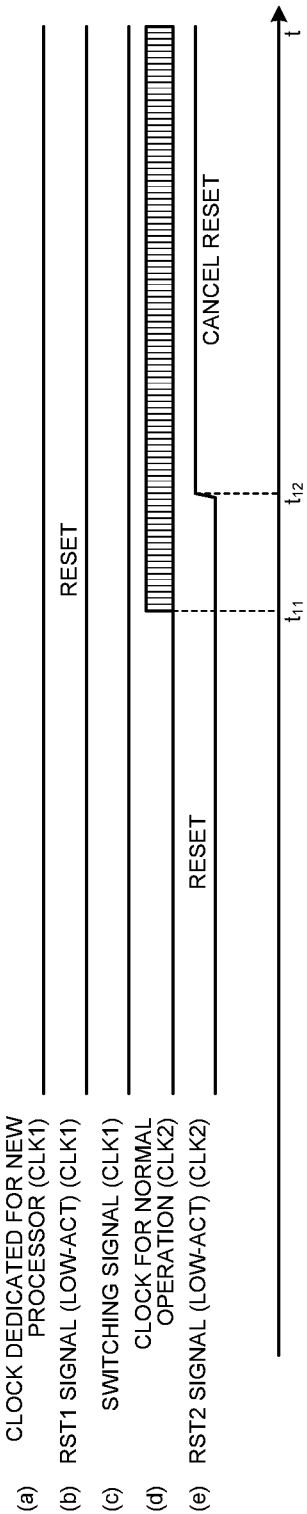
FIG. 6 is a timing chart illustrating the operation of each unit when the endoscope according to the first embodiment is coupled to the old processor.

Next, the operation timing of each unit of the endoscope 2 is described. FIG. 5 is a timing chart illustrating the operation of each unit when the endoscope 2 is coupled to the new processor 3. FIG. 6 is a timing chart illustrating the operation of each unit when the endoscope 2 is coupled to the old processor 5. In FIGS. 5 and 6, the horizontal axis represents time. In FIGS. 5 and 6, from the top side, (a) indicates the timing of the first clock signal (CLK1) input from the new processor 3, (b) indicates the timing of the first enable signal RST1 (Low-Act) (CLK1) output from the first generating unit 221, (c) indicates the timing of the switching signal (CLK1) output from the switching unit 223, (d) indicates the timing of the second clock signal (CLK2) input from the new processor 3 or the old processor 5, and (e) indicates the timing of the second enable signal RST2 (Low-Act) (CLK2) output from the second generating unit 222.

Operation when New Processor is Coupled

First, the operation timing when the endoscope 2 is coupled to the new processor 3 is described. As illustrated in FIG. 5, first, when the first clock signal is input from the new processor 3, the first generating unit 221 switches from the low state to the high state after the first clock signal becomes stable to cancel the reset state (time $t_1$) and output the first enable signal RST1 to the switching unit 223 (the time $t_1$).

Subsequently, the switching unit 223 switches from the low state to the high state based on the first enable signal RST1 input from the first generating unit 221 to set the operation mode from the old-processor coupling mode to the new-processor coupling mode (time $t_2$). In this case, the switching unit 223 outputs the switching signal to the TG 224 and the imaging signal processing unit 225 to switch from the old-processor coupling mode, which is the second operation mode previously set in the imaging unit 21 and the imaging signal processing unit 225, to the new-processor coupling mode, which is the first operation mode, and set the new-processor coupling mode.

Then, when the second clock signal is input from the new processor 3 (time $t_3$), the second generating unit 222 switches from the low state to the high state after the second clock signal becomes stable to cancel the reset state (time $t_4$) and output the second enable signal RST2 to the TG 224 and the imaging signal processing unit 225 so as to drive the TG 224 and the imaging signal processing unit 225. Accordingly, the endoscope 2 enters a state to enable the examination of the subject.

Operation when Old Processor is Coupled Next, the operation timing when the endoscope 2 is coupled to the old processor 5 is described. As illustrated in FIG. 6, as the first clock signal is not input from the new processor 3, the first generating unit 221 and the switching unit 223 are not in operation but maintain the reset state (the low state).

Then, when the second clock signal is input from the old processor 5 (time $t_{11}$), the second generating unit 222 switches from the low state to the high state after the second clock signal becomes stable to cancel the reset state (time $t_{12}$) and output the second enable signal RST2 to the TG 224 and the imaging signal processing unit 225 so as to drive the TG 224 and the imaging signal processing unit 225. Accordingly, the endoscope 2 enters a state to enable the examination of the subject.

According to the first embodiment described above, when the first clock signal is input from the new processor 3, the first generating unit 221 generates the first enable signal, which causes the switching unit 223 to output the switching signal, based on the first clock signal and outputs the first enable signal to the switching unit 223; thus, it is possible to switch the operation regardless of the type of processor and to achieve a further reduction in size.

According to the first embodiment, in a case where the first clock signal is input when the power of the endoscope 2 is activated, the first generating unit 221 outputs the first enable signal to the switching unit 223; thus, it is possible to switch the operation before the examination of the subject.

According to the first embodiment, in a case where the second clock signal is input when the power of the endoscope 2 is activated, the second generating unit 222 generates the second enable signal, which causes the TG 224 to operate in the second operation mode, based on the second clock signal and outputs the second enable signal to the TG 224; thus, even when the old processor 5 is coupled, the endoscope 2 may be driven.

Second Embodiment

Next, a second embodiment is described. Although the operation mode is switched depending on the type, the old processor or the new processor, according to the first embodiment described above, the communication mode is further switched depending on the type, the old processor or the new processor, according to the second embodiment. After the configuration of an endoscope system according to the second embodiment is described, the operation timing of each unit of an endoscope is described below.

Detailed Configuration of Endoscope System

Figure 7:
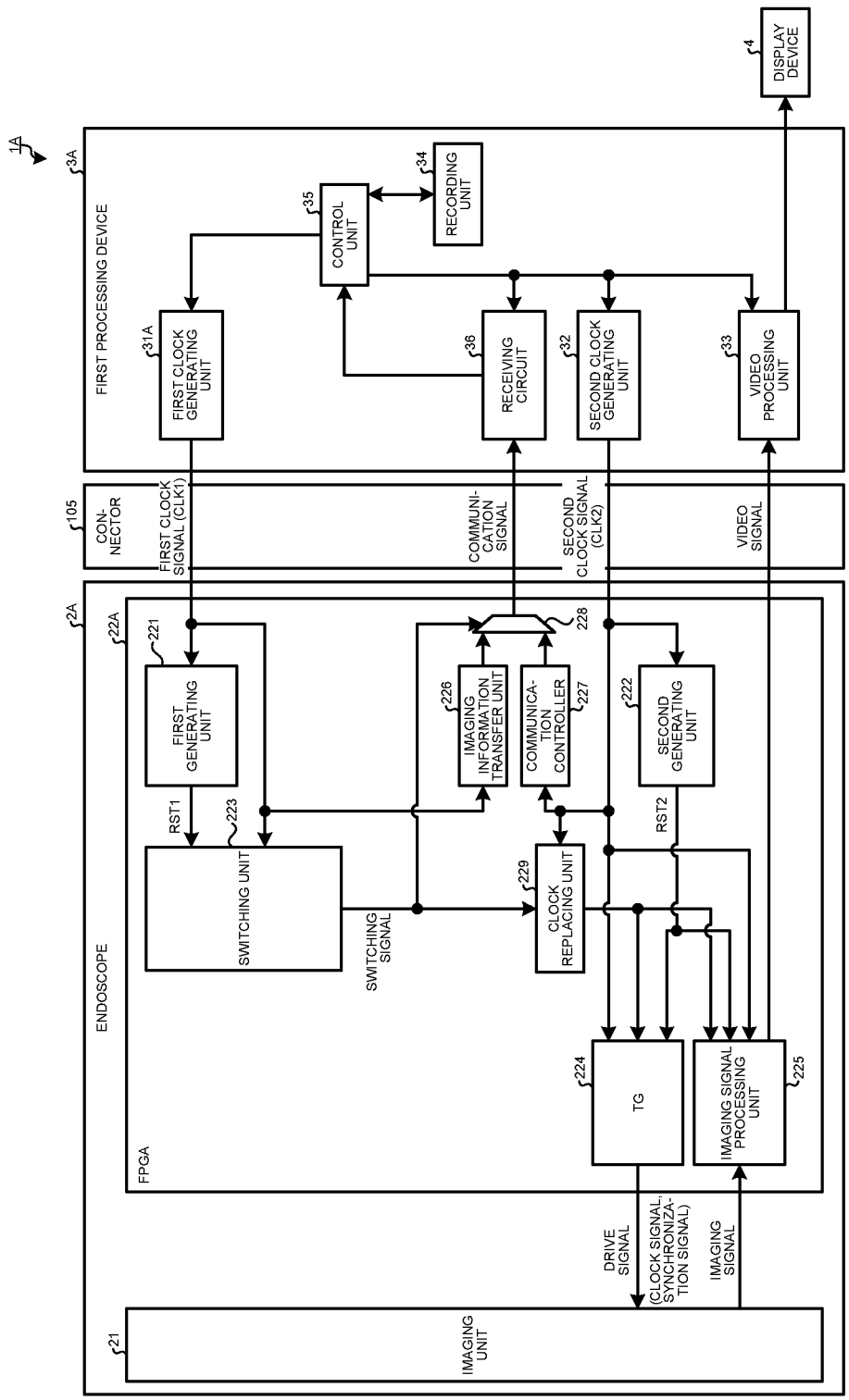
FIG. 7 is a block diagram illustrating a functional configuration in a state where the endoscope according to a second embodiment is coupled to a new processor.
Figure 8:
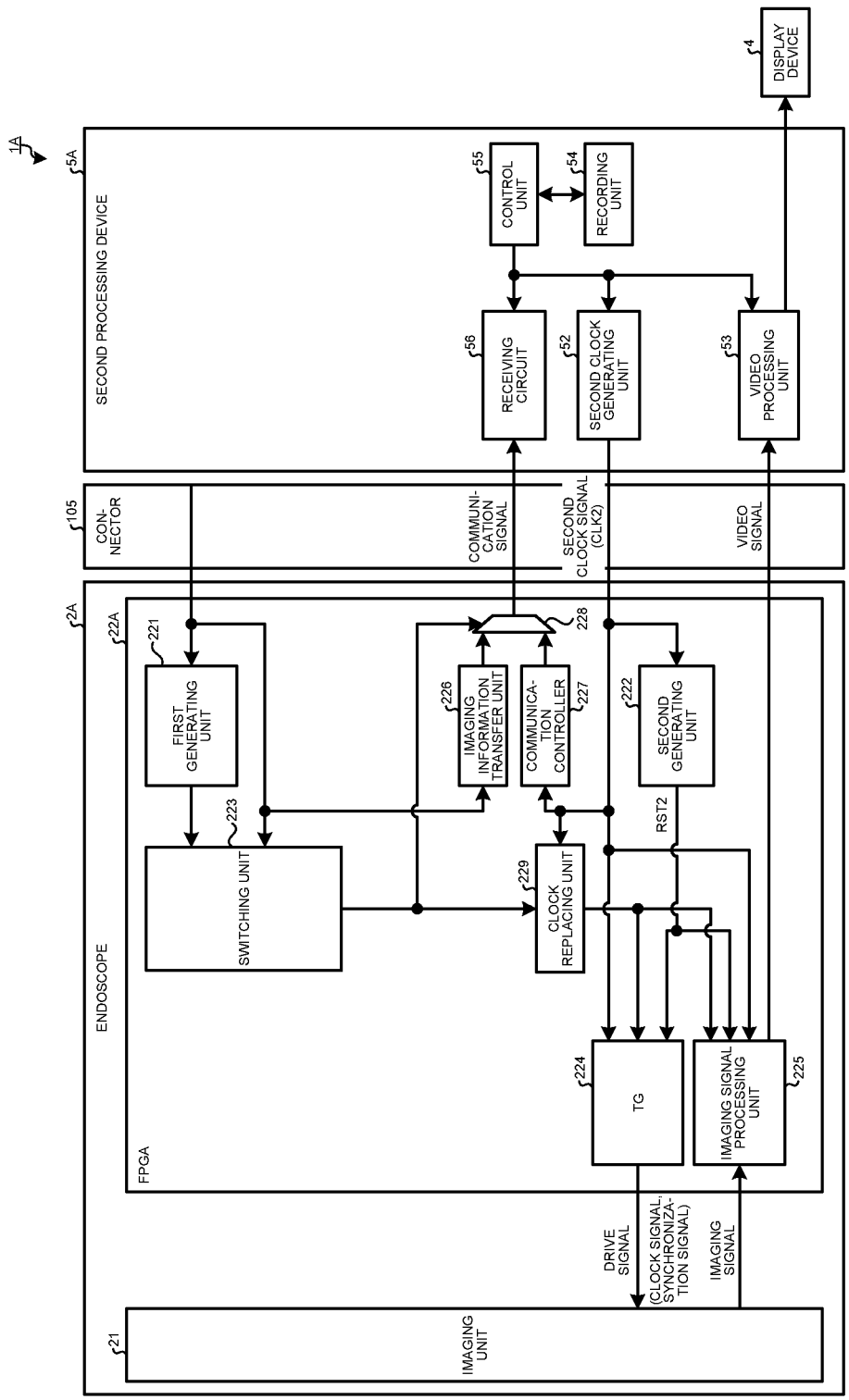
FIG. 8 is a block diagram illustrating a functional configuration in a state where the endoscope according to the second embodiment is coupled to an old processor.

FIG. 7 is a block diagram illustrating a functional configuration in a state where the endoscope according to the second embodiment is coupled to a new processor. FIG. 8 is a block diagram illustrating a functional configuration in a state where the endoscope according to the second embodiment is coupled to an old processor. An endoscope system 1A illustrated in FIGS. 7 and 8 includes at least an endoscope 2A, a new processor 3A, and an old processor 5A.

Configuration of Endoscope

First, the functional configuration of the endoscope 2A is described.

The endoscope 2A illustrated in FIG. 7 includes an FPGA 22A instead of the FPGA 22 in the endoscope 2 according to the first embodiment described above. The FPGA 22A further includes at least an imaging information transfer unit 226, a communication controller 227, a multiplexer 228, and a clock replacing unit 229, in addition to the configuration of the FPGA 22 according to the first embodiment described above.

The imaging information transfer unit 226 outputs, to the multiplexer 228, the identification signal for scope type ID information, operation clock information, power specification, etc., for the new processor 3A based on the dedicated first clock signal (CLK1) for transferring the imaging information, input from the new processor 3A.

The communication controller 227 outputs, to the multiplexer 228, various types of information regarding the endoscope 2A based on the second clock signal (CLK2) for the normal operation input from the new processor 3A or the old processor 5.

The multiplexer 228 outputs either one of the identification signal input from the imaging information transfer unit 226 and various types of information regarding the endoscope 2A input from the communication controller 227 to the new processor 3A or the old processor 5A coupled to the endoscope 2A on the basis of the switching signal input from the switching unit 223.

When the second clock signal is input in a case where the switching signal is input from the switching unit 223, the clock replacing unit 229 outputs the switching signal for operation in the second operation mode in accordance with the second clock signal to the TG 224 and the imaging signal processing unit 225. Specifically, when the switching signal is input from the switching unit 223, the clock replacing unit 229 replaces the switching signal generated in accordance with CLK1 input from the new processor 3A with the signal in accordance with CLK2 to hold the high/low state of the switching signal.

Configuration of New Processor

Next, the configuration of the new processor 3A is described.

The new processor 3A illustrated in FIG. 7 includes a first clock generating unit 31A instead of the first clock generating unit 31 in the new processor 3 according to the first embodiment described above. The new processor 3A further includes a receiving circuit 36 in addition to the configuration of the new processor 3 according to the first embodiment described above.

The first clock generating unit 31A generates the first clock signal (CLK1) having a predetermined frequency and outputs the first clock signal to the endoscope 2A under the control of the control unit 35. The first clock generating unit 31A is configured by using, for example, a clock generator.

The receiving circuit 36 outputs the identification signal or various types of information input from the coupled endoscope 2A to the control unit 35.

Configuration of Old Processor

Next, the functional configuration of the old processor 5 is described.

The old processor 5A illustrated in FIG. 8 includes a receiving circuit 56 in addition to the configuration of the old processor 5 according to the first embodiment described above.

The receiving circuit 56 outputs the identification signal or various types of information input from the coupled endoscope 2A to the control unit 55.

Operation Timing of Each Unit of Endoscope

Figure 9:
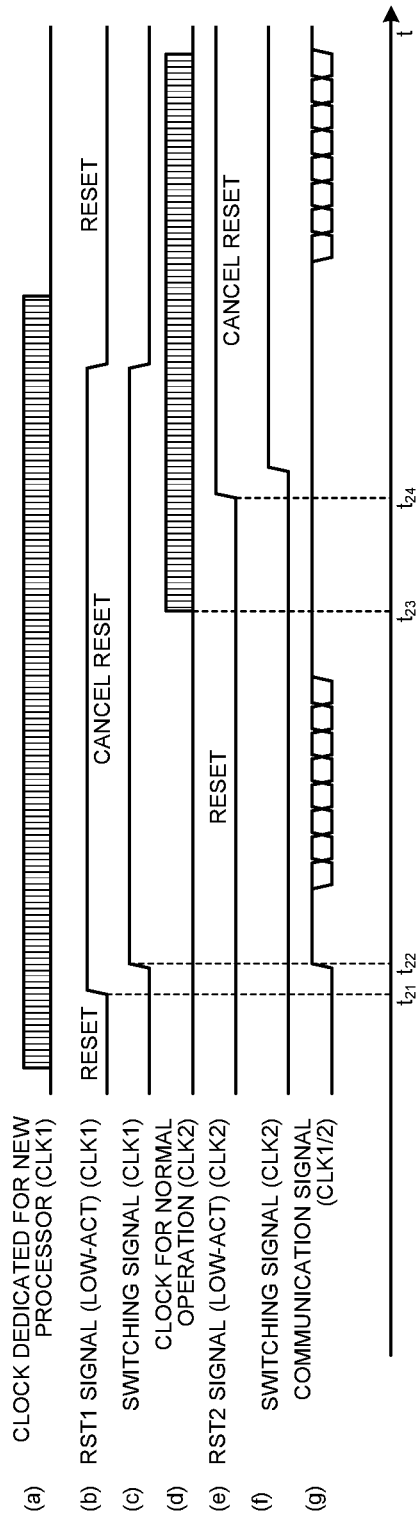
FIG. 9 is a timing chart illustrating the operation of each unit when the endoscope according to the second embodiment is coupled to the new processor.
Figure 10:
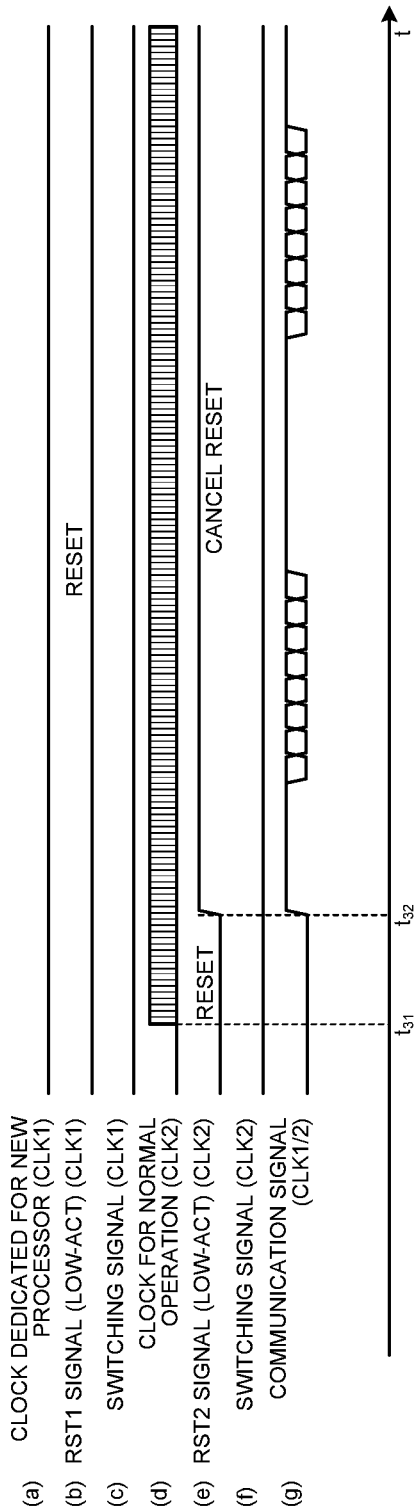
FIG. 10 is a timing chart illustrating the operation of each unit when the endoscope according to the second embodiment is coupled to the old processor.

Next, the operation timing of each unit of the endoscope 2A is described. FIG. 9 is a timing chart illustrating the operation of each unit when the endoscope 2A is coupled to the new processor 3A. FIG. 10 is a timing chart illustrating the operation of each unit when the endoscope 2A is coupled to the old processor 5A. In FIGS. 9 and 10, the horizontal axis represents time. In FIGS. 9 and 10, from the top side, (a) indicates the timing of the first clock signal (CLK1) input from the new processor 3A, (b) indicates the timing of the first enable signal RST1 (Low-Act) (CLK1) output from the first generating unit 221, (c) indicates the timing of the switching signal (CLK1) output from the switching unit 223, (d) indicates the timing of the second clock signal (CLK2)

input from the new processor 3A or the old processor 5A, (e) indicates the timing of the second enable signal RST2 (Low-Act) (CLK2) output from the second generating unit 222, (f) indicates the timing of the switching signal (CLK2), and (g) indicates the timing of a communication signal (CLK1/CLK2).

Operation when New Processor is Coupled First, the operation timing when the endoscope 2A is coupled to the new processor 3A is described. As illustrated in FIG. 9, first, when the dedicated first clock signal (CLK1) for transferring imaging information is input from the new processor 3A, the first generating unit 221 switches from the low state to the high state after the first clock signal becomes stable to cancel the reset state (time $t_2$) and output the first enable signal RST1 to the switching unit 223 (the time $t_{21}$).

Subsequently, the switching unit 223 switches from the low state to the high state based on the first enable signal RST1 input from the first generating unit 221 to set the operation mode from the old-processor coupling mode, which is the second operation mode, to the new-processor coupling mode, which is the first operation mode (time $t_{22}$). In this case, the switching unit 223 outputs the switching signal to the clock replacing unit 229. The multiplexer 228 outputs the identification signal input from the imaging information transfer unit 226 to the new processor 3A based on the switching signal input from the switching unit 223.

Then, when the second clock signal is input from the new processor 3 (time $t_{23}$), the second generating unit 222 switches from the low state to the high state after the second clock signal becomes stable to cancel the reset state (time $t_{24}$). Further, the clock replacing unit 229 replaces the switching signal with the second clock signal input from the new processor 3A or the old processor 5A and outputs the signal to the TG 224 and the imaging signal processing unit 225 (time $t_{24}$). In this case, the multiplexer 228 outputs various types of information regarding the endoscope 2A input from the communication controller 227 to the new processor 3A based on the switching signal input from the switching unit 223. Accordingly, the endoscope 2A enters a state to enable the examination of the subject. Further, each of the TG 224 and the imaging signal processing unit 225 is driven in accordance with the second clock signal (CLK) that is replaced by the clock replacing unit 229.

Operation when Old Processor is Coupled

Next, the operation timing when the endoscope 2A is coupled to the old processor 5A is described. As illustrated in FIG. 10, as the first clock signal is not input from the new processor 3A, the first generating unit 221 and the switching unit 223 are not in operation but maintain the reset state (the low state). Further, as the switching signal is not input from the switching unit 223, the clock replacing unit 229 maintains the low state as it does when the endoscope 2A is activated.

Then, when the second clock signal is input from the old processor 5 (time $t_{31}$), the second generating unit 222 switches from the low state to the high state after the second clock signal becomes stable to cancel the reset state (time $t_{32}$) and output the second enable signal RST2 to the TG 224 and the imaging signal processing unit 225 so as to drive the TG 224 and the imaging signal processing unit 225. Accordingly, the endoscope 2A enters a state to enable the examination of the subject.

According to the second embodiment described above, it is possible to switch the operation regardless of the type of processor and to achieve a further reduction in size, as in the first embodiment described above.

Third Embodiment

Next, a third embodiment is described. According to the third embodiment, a functional circuit provided in an endoscope is driven while two clock signals having different frequencies input from a new processor are switched. After the configuration of an endoscope system according to the third embodiment is described, the operation timing of each unit of the endoscope is described below. The same components as those of the endoscope system 1A according to the second embodiment described above are denoted by the same reference numeral, and detailed description thereof is omitted.

Detailed Configuration of Endoscope System

Figure 11:
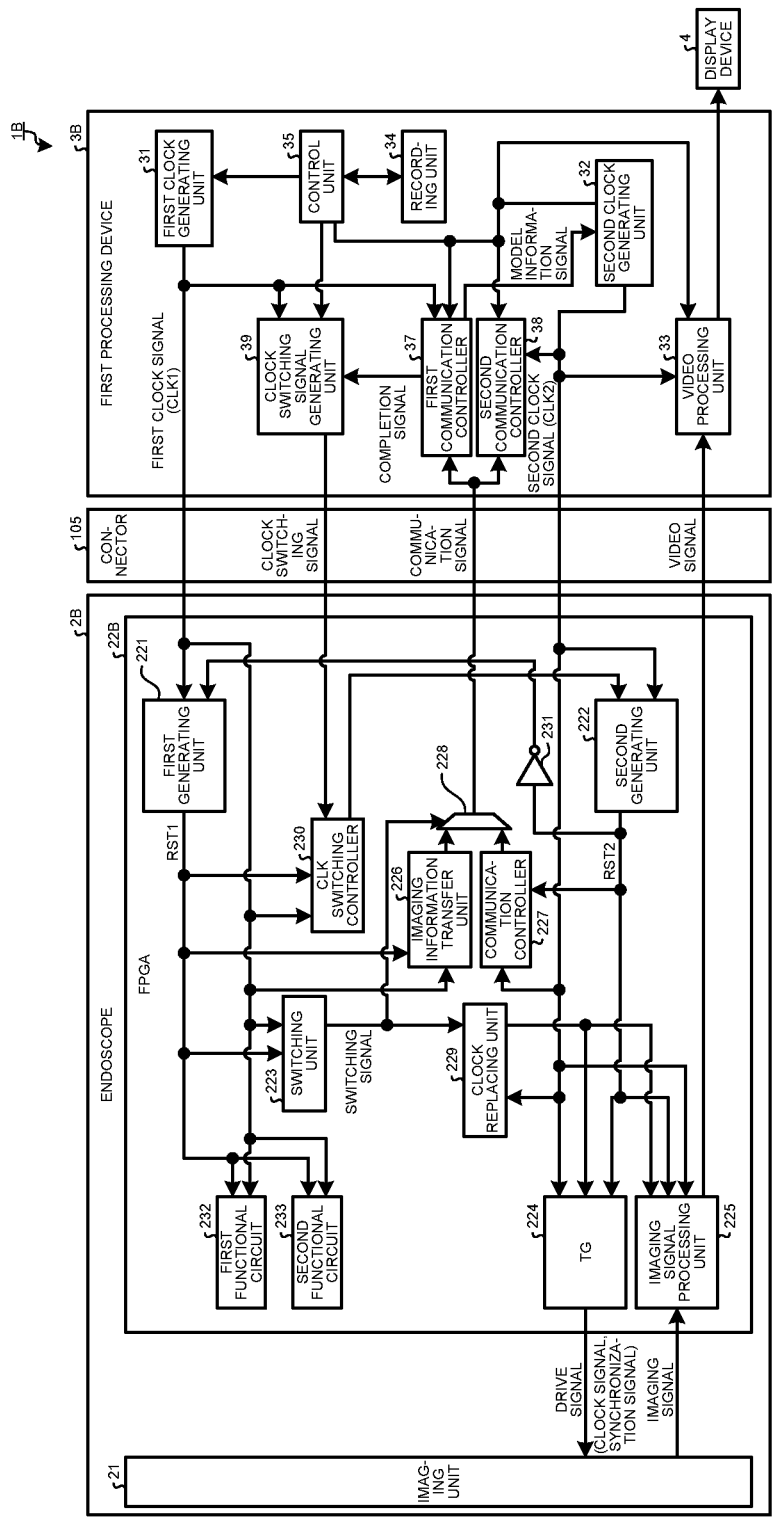
FIG. 11 is a block diagram illustrating a functional configuration of an endoscope system according to a third embodiment.

FIG. 11 is a block diagram illustrating a functional configuration of an endoscope system according to the third embodiment. An endoscope system 1B illustrated in FIG. 11 includes at least an endoscope 2B, a new processor 3B, and the display device 4. Although the endoscope 2B may be coupled to the old processors 5 and 5A described above in the first embodiment and the second embodiment, the endoscope 2B is coupled to the new processor 3B capable of outputting two clock signals having different frequencies in the following description.

Configuration of Endoscope

First, a functional configuration of the endoscope 2B is described.

The endoscope 2B illustrated in FIG. 11 includes an FPGA 22B instead of the FPGA 22A in the endoscope 2 according to the second embodiment described above. The FPGA 22B further includes a CLK switching controller 230, an inverter 231, a first functional circuit 232, and a second functional circuit 233 in addition to the configuration of the FPGA 22 according to the first embodiment described above.

The CLK switching controller 230 generates a second reset generation enable signal for controlling the second generating unit 222 based on the first clock signal input from the new processor 3B, the clock switching signal input from the new processor 3B, and the first enable signal RST1 input from the first generating unit 221 and outputs the reset generation enable signal to the second generating unit 222.

The inverter 231 outputs, to the first generating unit 221, a first reset generation enable signal obtained by inverting the voltage level of the second enable signal RST2 input from the second generating unit 222.

The first functional circuit 232 is driven with the first clock signal (CLK1). The first functional circuit 232 is, for example, an abnormality detection circuit that detects an abnormality such as overcurrent or overvoltage in the endoscope 2B that operates in synchronization with the first clock signal, or a power sequence circuit that controls a power activation timing in the endoscope 2B.

The second functional circuit 233 is driven with the second clock signal (CLK2). The second functional circuit 233 is, for example, an abnormality detection circuit that detects an abnormality such as overcurrent or overvoltage in the endoscope 2B that operates in synchronization with the second clock signal, or a power sequence circuit that controls a power activation timing in the endoscope 2B.

Configuration of New Processor

Next, a functional configuration of the new processor 3B is described.

The new processor 3B illustrated in FIG. 11 further includes a first communication controller 37, a second communication controller 38, and a clock switching signal generating unit 39 in addition to the configuration of the new processor 3A according to the second embodiment described above.

The first communication controller 37 outputs, to the clock switching signal generating unit 39, a completion signal indicating that the operation mode of the endoscope 2B has been switched. The first communication controller 37 is configured by using a communication module.

The second communication controller 38 outputs a model information signal indicating the model information on the coupled endoscope 2B to the second clock generating unit 32. The second communication controller 38 is configured by using a communication module.

The clock switching signal generating unit 39 outputs a clock switching enable signal to the endoscope 2B based on the completion signal input from the first communication controller 37.

Process of Endoscope System

Figure 12:
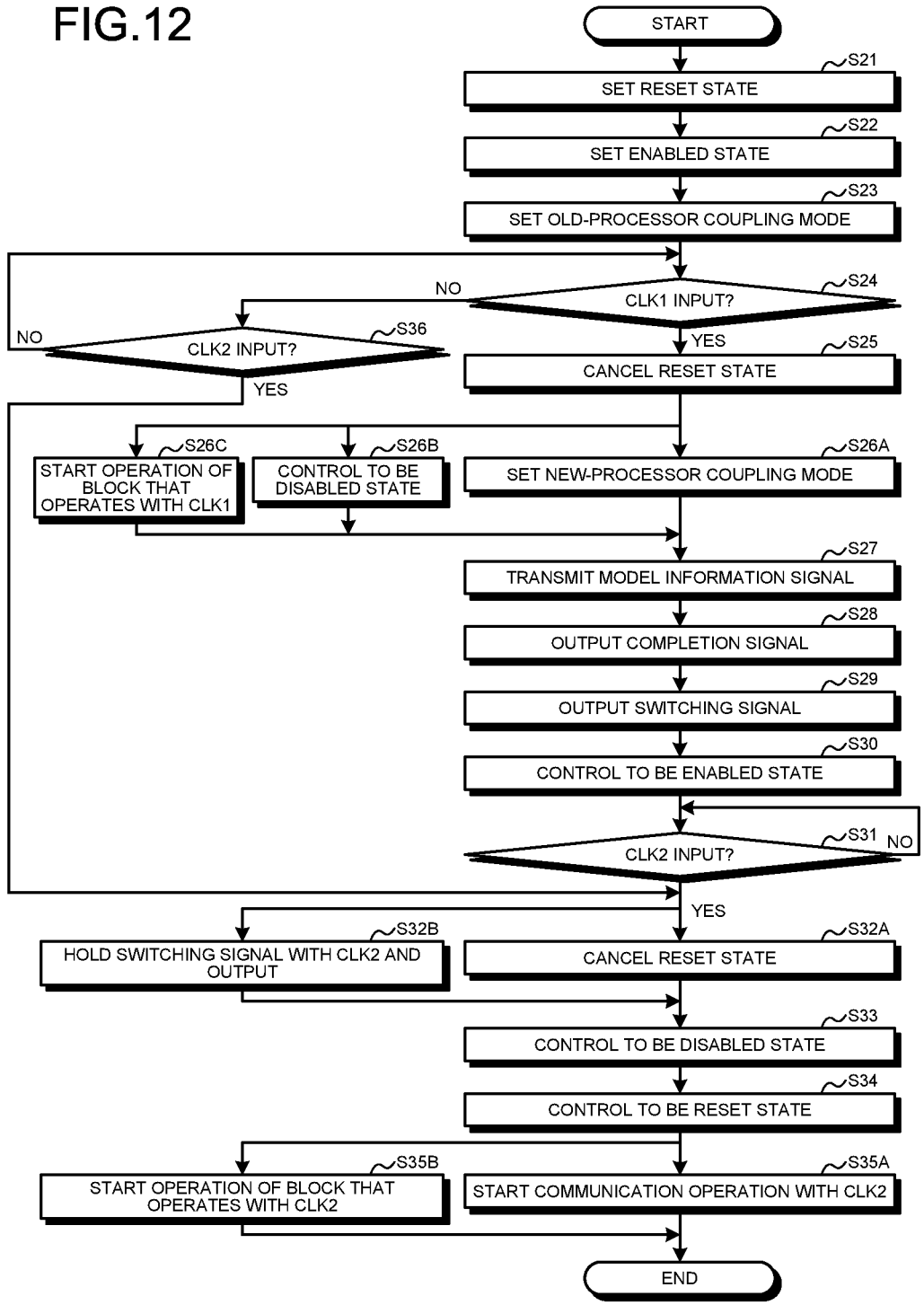
FIG. 12 is a flowchart illustrating the overview of a process performed by the endoscope system according to the third embodiment.

Next, a process performed by the endoscope system 1B is described. FIG. 12 is a flowchart illustrating the overview of the process performed by the endoscope system 1B.

As illustrated in FIG. 12, first, when the power of the endoscope 2B is activated, the first generating unit 221 and the second generating unit 222 each set their own states to the reset state (Step S21).

Subsequently, the CLK switching controller 230 and the inverter 231 each sets their own states to an enabled state (Step S22).

Then, the switching unit 223 sets the operation mode to the old-processor coupling mode that is the second operation mode (Step S23).

Subsequently, when the first clock signal (CLK1) is input from the new processor 3B (Step S24: Yes) as the new processor 3B is coupled, the endoscope system 1B proceeds to Step S25 described below. Conversely, when the first clock signal (CLK1) is not input from the new processor 3B (Step S24: No) as the new processor 3B is not coupled but the old processor 5 is coupled and the second clock signal (CLK2) is not also input (Step S36: No), the endoscope system 1B returns to Step S24 described above. When the first clock signal (CLK1) is not input from the new processor 3B (Step S24: No) and the second clock signal (CLK2) is input (Step S36: Yes) as the new processor 3B is not coupled but the old processor 5 is coupled, the endoscope system 1B proceeds to Step S32A and Step S32B described below.

At Step S25, the first generating unit 221 cancels the reset state based on the first clock signal (CLK1) input from the new processor 3B to generate and output the first enable signal RST1 to the switching unit 223, the CLK switching controller 230, the imaging information transfer unit 226, the first functional circuit 232, and the second functional circuit 233.

Subsequently, the switching unit 223 generates the switching signal for switching the imaging unit 21 to the new-processor coupling mode, which is the first operation mode, based on the first enable signal RST1 input from the first generating unit 221 and the first clock signal (CLK1) input from the new processor 3 and outputs the generated switching signal to the clock replacing unit 229 (Step S26A). In this case, the CLK switching controller 230 controls its own state to be a disabled state (Step S26B). The first functional circuit 232 and the second functional circuit 233 start an operation based on the first clock signal and the first enable signal RST1 (Step S26C).

Then, the imaging information transfer unit 226 transmits the model information signal regarding the type of the imaging unit 21 to the new processor 3B via the multiplexer 228 (Step S27).

Subsequently, the first communication controller 37 outputs the completion signal indicating that the model information signal has been received from the imaging information transfer unit 226 to the clock switching signal generating unit 39 (Step S28).

Then, the clock switching signal generating unit 39 outputs a clock switching signal to the CLK switching controller 230 of the endoscope 2B (Step S29).

The CLK switching controller 230 outputs an RST2 generation enable signal to the second generating unit 222 to control the state of the second generating unit 222 so as to be an enabled state (Step S30). After Step S30, the endoscope system 1B proceeds to Step S31 described below.

At Step S31, when the second clock signal (CLK2) is input from the new processor 3B or the old processor 5 (Step S31: Yes), the endoscope system 1B proceeds to Step S32A and Step S32B described below. Conversely, when the second clock signal (CLK2) is not input from the new processor 3B or the old processor 5 (Step S31: No), the endoscope system 1B waits until the second clock signal (CLK2) is input.

After Step S31, the second generating unit 222 cancels the reset state based on the second clock signal to generate and output the second enable signal RST2 to the TG 224 and the imaging signal processing unit 225 (Step S32A). In this case, the clock replacing unit 229 holds the high/low state of the switching signal with the second clock signal and outputs the signal to the TG 224 and the imaging signal processing unit 225 (Step S32B).

Subsequently, the second generating unit 222 outputs the second enable signal RST2 to the inverter 231 to control the inverter 231 so as to be in a disabled state (Step S33).

Then, the inverter 231 outputs an RST1 generation enable signal to the first generating unit 221 to control the state of the first generating unit 221 so as to be the reset state (Step S34).

Subsequently, the communication controller 227 starts a communication operation using the second clock signal (CLK2) via the multiplexer 228 (Step S35A). In this case, the second generating unit 222 generates and outputs the second enable signal RST2 to the TG 224 and the imaging signal processing unit 225 so that the TG 224 and the imaging signal processing unit 225 may operate with the second clock signal (CLK2). After Step S35A and Step S35B, the endoscope system 1B ends this process. Accordingly, the endoscope system 1B may execute the examination of the subject.

According to the third embodiment described above, it is possible to switch the operation regardless of the type of processor and to achieve a further reduction in size, as in the first embodiment described above.

Fourth Embodiment

Next, a fourth embodiment is described. According to the fourth embodiment, a functional circuit provided in an endoscope is driven while two clock signals having different frequencies input from a new processor are switched. After the configuration of an endoscope system according to the fourth embodiment is described, the operation timing of the endoscope system is described below. The same components as those in the endoscope system 1B according to the third embodiment described above are denoted by the same reference numeral, and detailed description thereof is omitted.

Detailed Configuration of Endoscope System

Figure 13:
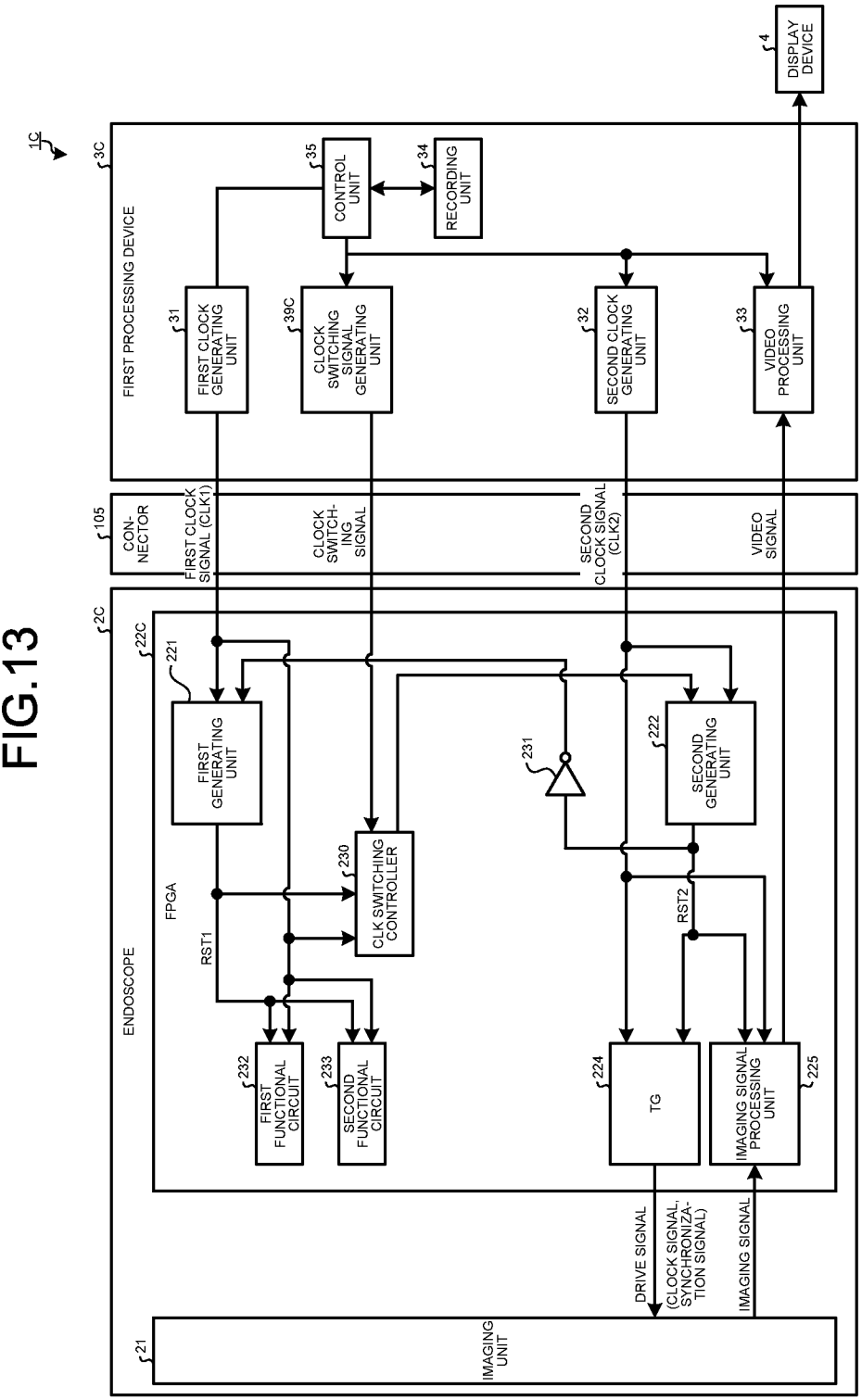
FIG. 13 is a block diagram illustrating a functional configuration of an endoscope system according to a fourth embodiment.

FIG. 13 is a block diagram illustrating a functional configuration of the endoscope system according to the fourth embodiment. An endoscope system 1C illustrated in FIG. 13 includes at least an endoscope 2C, a new processor 3C, and the display device 4.

Configuration of Endoscope

First, a functional configuration of the endoscope 2C is described.

The endoscope 2C illustrated in FIG. 13 includes an FPGA 22C instead of the FPGA 22B according to the third embodiment described above. In the FPGA 22C, the switching unit 223, the imaging information transfer unit 226, the communication controller 227, the multiplexer 228, and the clock replacing unit 229 included in the FPGA 22B according to the third embodiment described above are omitted.

Configuration of New Processor

Next, the configuration of the new processor 3C is described.

In the new processor 3C, the first communication controller 37 and the second communication controller 38 included in the new processor 3B according to the third embodiment described above are omitted.

Process of Endoscope System

Figure 14:
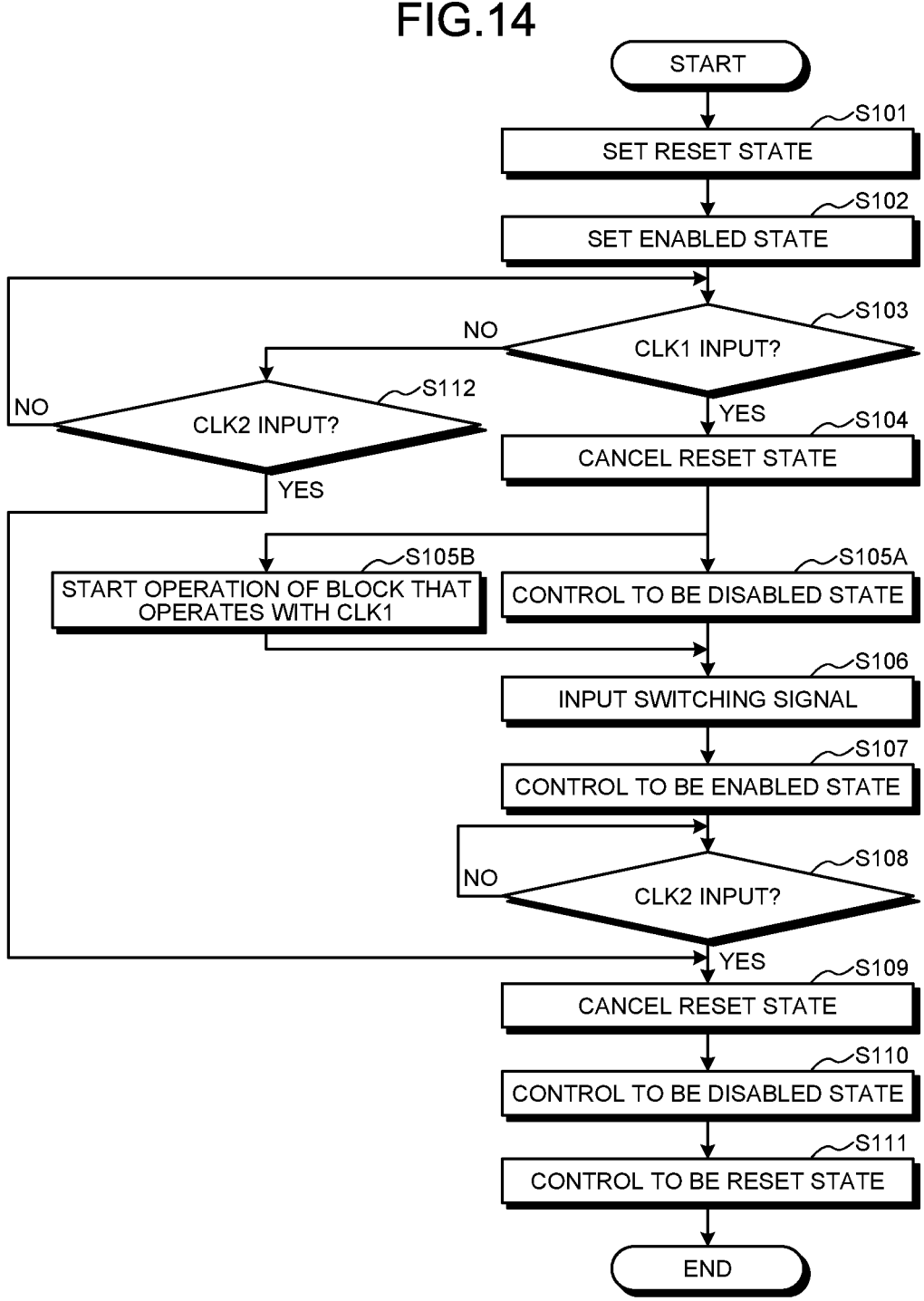
FIG. 14 is a flowchart illustrating the overview of a process performed by the endoscope system according to the fourth embodiment.

Next, the process performed by the endoscope system 10 is described. FIG. 14 is a flowchart illustrating the overview of the process performed by the endoscope system 10.

As illustrated in FIG. 14, first, when the power of the endoscope 2C is activated, the first generating unit 221 and the second generating unit 222 each set their own states to the reset state (Step S101).

Subsequently, the CLK switching controller 230 and the inverter 231 each set their states to an enabled state (Step S102).

Subsequently, when the first clock signal (CLK1) is input from the new processor 3C (Step S103: Yes) as the new processor 3C is coupled, the endoscope system 10 proceeds to Step S104 described below. Conversely, when the first clock signal (CLK1) is not input from the new processor 3C (Step S103: No) as the new processor 3C is not coupled but the old processor 5 is coupled and the second clock signal (CLK2) is not also input (Step S112: No), the endoscope system 10 returns to Step S103 described above. When the first clock signal (CLK1) is not input from the new processor 3C (Step S103: No) and the second clock signal (CLK2) is input (Step S112: Yes) as the new processor 3C is not coupled but the old processor 5 is coupled, the endoscope system 10 proceeds to Step S109 described below.

At Step S104, the first generating unit 221 cancels the reset state based on the first clock signal (CLK1) input from the new processor 3C to generate and output the first enable signal RST1 to the CLK switching controller 230, the first functional circuit 232, and the second functional circuit 233.

Subsequently, the CLK switching controller 230 controls its own state so as to be a disabled state (Step S105A). In this case, the first functional circuit 232 and the second functional circuit 233 start an operation based on the first clock signal and the first enable signal RST1 (Step S105B).

Then, the CLK switching controller 230 receives the input clock switching signal, input from a clock switching signal generating unit 39C of the new processor 3A (Step S106) and outputs the RST2 generation enable signal to the second generating unit 222 to control the state of the second generating unit 222 so as to be an enabled state (Step S107). After Step S107, the endoscope system 1 proceeds to Step S108 described below.

At Step S108, when the second clock signal (CLK2) is input from the new processor 3C or the old processor 5 (Step S108: Yes), the endoscope system 10 proceeds to Step S109 described below. Conversely, when the second clock signal (CLK2) is not input from the new processor 3C or the old processor 5 (Step S108: No), the endoscope system 10 waits until the second clock signal (CLK2) is input.

At Step S109, the second generating unit 222 cancels the reset state based on the second clock signal to generate and output the second enable signal RST2 to the TG 224 and the imaging signal processing unit 225.

Subsequently, the second generating unit 222 outputs the second enable signal RST2 to the inverter 231 to control the inverter 231 so as to be in a disabled state (Step S110).

Subsequently, the inverter 231 outputs the RST1 generation enable signal to the first generating unit 221 to control the first generating unit 221 so as to be in a reset state (Step S111). After Step S111, the endoscope system 10 ends this process. Accordingly, the endoscope system 10 may execute the examination of the subject.

Operation Timing of Each Unit of Endoscope

Figure 15:
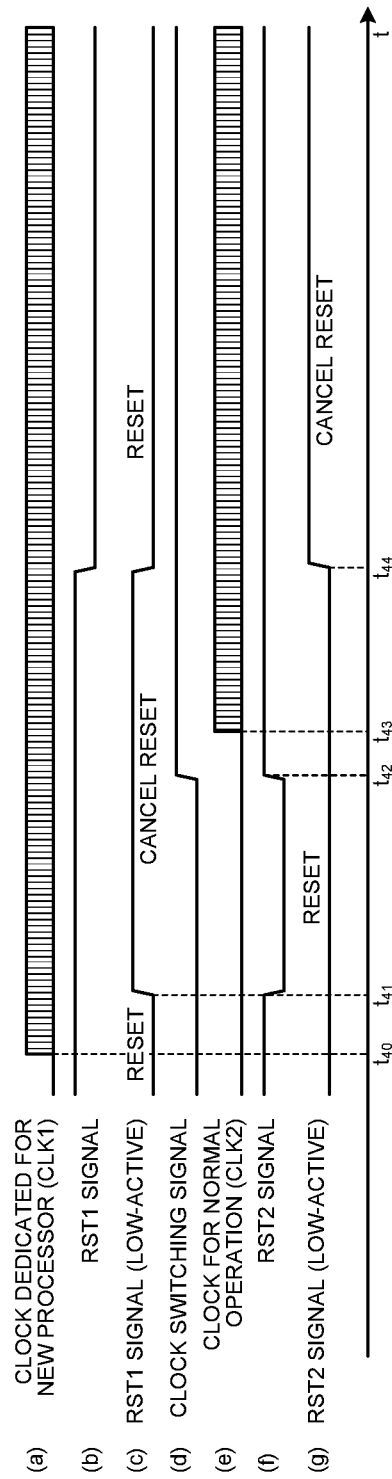
FIG. 15 is a timing chart illustrating the operation of each unit when an endoscope according to the fourth embodiment is coupled to a new processor.
Figure 16:
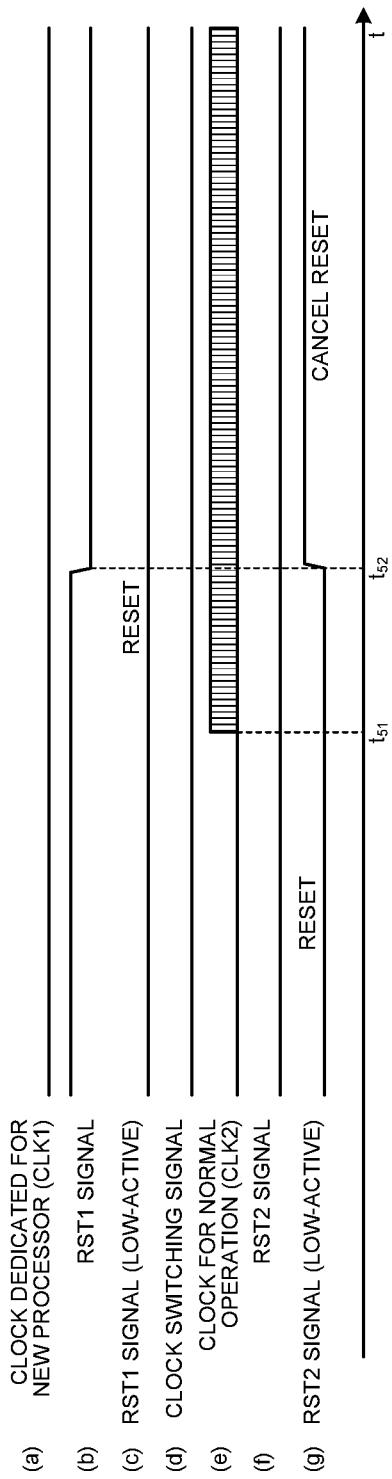
FIG. 16 is a timing chart illustrating the operation of each unit when the endoscope according to the fourth embodiment is coupled to an old processor.

Next, the operation timing of each unit of the endoscope 2C is described. FIG. 15 is a timing chart illustrating the operation of each unit when the endoscope 2C is coupled to the new processor 3C. FIG. 16 is a timing chart illustrating the operation of each unit when the endoscope 2C is coupled to the old processor 5. In FIGS. 15 and 16, the horizontal axis represents time. In FIGS. 15 and 16, from the top side, (a) indicates the timing of the first clock signal (CLK1) input from the new processor 3C, (b) indicates the operation timing of the output signal from the inverter 231, (c) indicates the timing of the RST1 signal (Low-Act) output from the first generating unit 221, (d) indicates the timing of the clock switching signal input from the new processor 3C, (e) indicates the timing of the second clock signal (CLK2) input from the new processor 3C or the old processor 5, (f) indicates the operation timing of the output signal from the CLK switching controller 230, and (g) indicates the timing of the RST2 signal (Low-Act) (CLK2) output from the second generating unit 222.

Operation when New Processor is Coupled First, the operation timing when the endoscope 2C is coupled to the new processor 3C is described. As illustrated in FIG. 15, when the power of the endoscope 2C is turned on and the endoscope 2C is activated, the CLK switching controller 230 and the inverter 231 are in an enabled state (high state).

First, when the first clock signal is input from the new processor 3C (time $t_{40}$), the first generating unit 221 switches from the low state to the high state after the first clock signal becomes stable to cancel the reset state (time $t_{41}$) and output the first enable signal RST1 to the CLK switching controller 230. Accordingly, the CLK switching controller 230 transitions from the enabled state (high state) to the reset state. In this case, when the second clock signal is input to the endoscope 2C, and even if a noise is superimposed on the second clock signal, the control is performed not to perform the reset cancellation operation in the endoscope 2C.

Subsequently, when the clock switching signal is input from the new processor 3C (time $t_{42}$), the CLK switching controller 230 transitions from the low state to the high state (the time $t_{42}$).

Then, when the second clock signal is input from the new processor 3C (time $t_{43}$), the second generating unit 222 switches from the low state to the high state after the second clock signal becomes stable to cancel the reset state (time $t_{44}$) and output the second enable signal RST2 to the TG 224, the imaging signal processing unit 225, and the inverter 231. Accordingly, the inverter 231 outputs the RST generation enable signal to the first generating unit 221. Specifically, the first generating unit 221 receives the second enable signal RST2 input from the second generating unit 222 to transition to the reset state (low state). Accordingly, the endoscope 2C enters a state to enable the examination of the subject.

Operation when Old Processor is Coupled

Next, the operation timing when the endoscope 2C is coupled to the old processor 5 (a processor that exclusively outputs a unit clock) is described.

As illustrated in FIG. 16, as the first clock signal is not input from the old processor 5, the inverter 231 is in an enabled state (high state) when the power of the endoscope 2C is turned on and the endoscope 2C is activated.

Then, when the second clock signal is input from the old processor 5 (time $t_{51}$), the second generating unit 222 switches from the low state to the high state after the second clock signal becomes stable to cancel the reset state (time $t_{52}$) and output the second enable signal to the TG 224, the imaging signal processing unit 225, and the inverter 231. Accordingly, the inverter 231 outputs the RST generation enable signal to the first generating unit 221. Specifically, the first generating unit 221 receives the second enable signal RST2 input from the second generating unit 222 to transition to the reset state (low state). Accordingly, the endoscope 2C enters a state to enable the examination of the subject.

According to the fourth embodiment described above, as it is possible to prevent improper recognition due to the noise included in the clock line with no input, the FPGA 22C may be accurately operated.

Fifth Embodiment

Next, a fifth embodiment is described. According to the fifth embodiment, when the input first clock signal is received by an endoscope and is switched to the second clock signal, an enable signal is received in both directions. An endoscope system according to the fifth embodiment is described below. The same components as those in the endoscope system according to the above-described fourth embodiment are denoted by the same reference numeral, and detailed description thereof is omitted.

Configuration of Endoscope System

Figure 17:
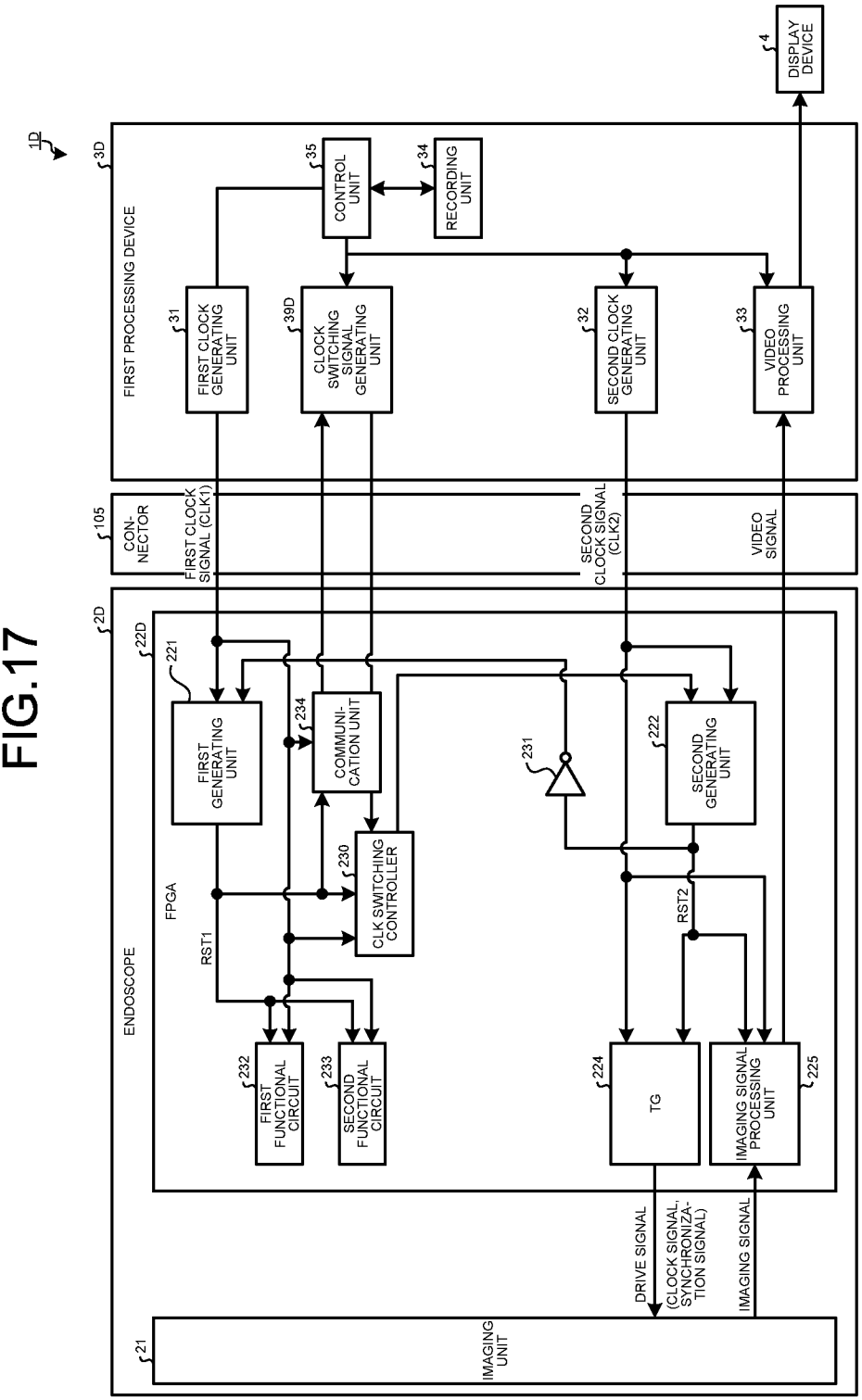
FIG. 17 is a block diagram illustrating a functional configuration of an endoscope system according to a fifth embodiment.

FIG. 17 is a block diagram illustrating a functional configuration of the endoscope system according to the fifth embodiment. An endoscope system 1D illustrated in FIG. 17 includes at least an endoscope 2D, a new processor 3D, and the display device 4.

Configuration of Endoscope

First, a functional configuration of the endoscope 2D is described.

The endoscope 2D illustrated in FIG. 17 includes an FPGA 22D instead of the FPGA 22C according to the fourth embodiment described above. The FPGA 22D further includes a communication unit 234 (communicator) in addition to the configuration of the FPGA 22C according to the above-described third embodiment.

The communication unit 234 receives a clock-signal switching enable signal from the new processor 3D and outputs a completion signal indicating reset completion to the new processor 3D. The communication unit 234 outputs the clock-signal switching enable signal received from the new processor 3D to the CLK switching controller 230.

Configuration of New Processor

Next, the configuration of the new processor 3 is described.

The new processor 3D includes a clock switching signal generating unit 39D instead of the clock switching signal generating unit 39C in the new processor 3C according to the fourth embodiment described above.

The clock switching signal generating unit 39D transmits the clock-signal switching enable signal to the communication unit 234 and receives the completion signal from the communication unit 234.

The endoscope system 1D having the above configuration performs the same process as that of the endoscope system 10 according to the fourth embodiment described above so that the enable signal is output when the input first clock signal is received by the endoscope 2D and is switched to the second clock signal. Thus, it is possible to prevent improper recognition due to the noise included in the clock line with no input, and therefore the FPGA 22C may be accurately operated.

According to the fifth embodiment described above, as it is possible to prevent improper recognition due to the noise included in the clock line with no input, the FPGA 22C may be accurately operated.

Various embodiments may be implemented by appropriately combining the components disclosed in the endoscope system according to the above-described embodiment of the present disclosure. For example, some components may be deleted from all the components described in the endoscope system according to the above-described embodiment of the present disclosure. Further, the components described in the endoscope system according to the above-described embodiment of the present disclosure may be combined as appropriate.

In the endoscope system according to the embodiment of the present disclosure, the "unit" described above may be read as "means", "circuit", or the like. For example, the control unit may be read as a control means or a control circuit.

The program to be executed by the endoscope system according to the embodiment of the present disclosure is provided by being recorded in a computer-readable recording medium such as a CD-ROM, a flexible disk (FD), a CD-R, a digital versatile disk (DVD), a USB medium, or a flash memory in an installable form or an executable form of file data.

A configuration may be such that the program to be executed by the endoscope system according to the embodiment of the present disclosure is stored in a computer connected via a network, such as the Internet, and provided by being downloaded via the network.

Although the order of the processes at the steps is described by using expressions such as "first", "subsequently", or "then" in the explanation of the flowchart in this description, the order of the processes necessary for carrying out the disclosure is not uniquely defined by the expressions. That is, the order of the processes in the flowchart described in this description may be changed to such a degree that there is no contradiction. Further, instead of the program including the simple branching processing described above, a larger number of determination items may be comprehensively evaluated for branching. In this case, it is possible to simultaneously use a technique of artificial intelligence for machine learning that prompts the user to perform a manual operation and repeatedly executes learning. Moreover, it is also possible to execute deep learning by learning an operation pattern performed by many experts and inputting more complicated conditions.

According to the present disclosure, it is possible to produce an advantage such that an operation may be switched regardless of the type of processing device.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope that detachably couples to a first processor outputting a first clock signal and a second clock signal and a second processor outputting a second clock signal, the endoscope comprising:
an integrated circuit configured to:
in a first operation mode:
receive the first clock signal and the second clock signal from the first processor;
switch from a first state to a second state in response to the first clock signal received;
generate a first enable signal based on the first clock signal while in the second state;
generate a switching signal based on the first enable signal and the first clock signal; and
generate a first drive signal for driving the endoscope based on the switching signal and the second clock signal received from the first processor; and
in a second operation mode:
receive the second clock signal from the second processor; and
in the absence of the first clock signal from the first processor, generate a second drive signal for driving the endoscope based on the second clock signal received from the second processor.

2. The endoscope according to claim 1,
wherein the integrated circuit is configured to switch from the first state to the second state in response to the first clock signal received when a power of the endoscope is activated.

3. The endoscope according to claim 1,
wherein the integrated circuit is further configured to:
disable the second clock signal received from the second processor when a power of the endoscope is activated; and
enable the second clock signal received from the second processor when a clock switching signal for switching from the first clock signal to the second clock signal is received from the first processor.

4. The endoscope according to claim 3,
wherein the integrated circuit is further configured to:
communicate with the first processor; and
enable the second clock signal received from the first processor at a receiving timing when the clock switching signal is received.

5. The endoscope according to claim 4,
wherein the integrated circuit is configured to enable the second clock signal received from the first processor after input of the first clock signal is overlapped with input of the second clock signal for a predetermined time period.

6. The endoscope according to claim 5,
wherein the integrated circuit is configured to operate the endoscope in the first operation mode in accordance with the first drive signal when the second clock signal is received from the first processor in a case where the clock switching signal is received.

7. The endoscope according to claim 1, further comprising:
an image sensor,
wherein the image sensor is configured to generate an imaging signal based on the first drive signal.

8. The endoscope according to claim 1,
wherein the integrated circuit is configured to:
in the first operation mode:
switch from a third state to a fourth state in response to the second clock signal received from the first processor;
generate a second enable signal while in the fourth state;
generate the first drive signal based on the switching signal, the second enable signal and the second clock signal received from the first processor; and
in the second operation mode:
switch from the third state to the fourth state in response to the second clock signal received from the second processor;
generate the second enable signal while in the fourth state; and
in the absence of the first clock signal from the first processor, generate the second drive signal based on the second enable signal and second clock signal received from the second processor.

9. The endoscope according to claim 1,
wherein the integrated circuit is configured to output one of an identification signal and various types of information to one of the first processor and the second processor based on the second clock signal received from one of the first processor and the second processor.

10. A driving method implemented by an endoscope that detachably couples to a first processor outputting a first clock signal and a second clock signal and a second processor outputting a second clock signal, the driving method comprising:
in a first operation mode:
receiving the first clock signal and the second clock signal from the first processor; switching from a first state to a second state in response to the first clock signal received;
generating a first enable signal based on the first clock signal while in the second state;
generating a switching signal based on the first enable signal and the first clock signal; and
generating a first drive signal for driving the endoscope based on the switching signal and the second clock signal received from the first processor; and
in a second operation mode:
receiving the second clock signal from the second processor; and
in the absence of the first clock signal from the first processor, generating a second drive signal for driving the endoscope based on the second clock signal received from the second processor.

11. The driving method according to claim 10, further comprising:

switching from the first state to the second state in response to the first clock signal received when a power of the endoscope is activated.

12. The driving method according to claim 10, further comprising:
disabling the second clock signal received from the second processor when a power of the endoscope is activated; and
enabling the second clock signal received from the second processor when a clock switching signal for switching from the first clock signal to the second clock signal is received from the first processor.

13. The driving method according to claim 10, further comprising:
in the first operation mode:
switching from a third state to a fourth state in response to the second clock signal received from the first processor;
generating a second enable signal while in the fourth state;
generating the first drive signal based on the switching signal, the second enable signal and the second clock signal received from the first processor; and
in the second operation mode:
switching from the third state to the fourth state in response to the second clock signal received from the second processor;
generating the second enable signal while in the fourth state; and
in the absence of the first clock signal from the first processor, generating the second drive signal for driving the endoscope based on the second enable signal and second clock signal received from the second processor.

14. An endoscope system comprising
a first processor configured to output a first clock signal and a second clock signal; and
an endoscope configured to detachably couple to the first processor and a second processor outputting a second clock signal, the endoscope comprising:
an image sensor; and
an integrated circuit configured to:
in a first operation mode:
receive the first clock signal and the second clock signal from the first processor;
switch from a first state to a second state in response to the first clock signal received;
generate a first enable signal based on the first clock signal while in the second state;
generate a switching signal based on the first enable signal and the first clock signal; and
generate a first drive signal for driving the endoscope based on the switching signal and the second clock signal received from the first processor; and
in a second operation mode:
receive the second clock signal from the second processor; and
in the absence of the first clock signal from the first processor, generate a second drive signal for driving the endoscope based on the second clock signal received from the second processor.

15. The endoscope system according to claim 14, wherein the integrated circuit is configured to switch from the first state to the second state in response to the first clock signal received when a power of the endoscope is activated.

16. A system comprising:
the endoscope according to claim 1;
the first processor; and
the second processor.

* * * * *